US011534403B2

(12) United States Patent
Badiali et al.

(10) Patent No.: US 11,534,403 B2
(45) Date of Patent: *Dec. 27, 2022

(54) LIQUID PHARMACEUTICAL COMPOSITION

(71) Applicant: Arecor Limited, Saffron Walden (GB)

(72) Inventors: Luca Badiali, Milton (GB); David Gerring, Haslingfield (GB); Jan Jezek, Saffron Walden (GB)

(73) Assignee: ARECOR LIMITED, Saffron Walden (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/491,506

(22) PCT Filed: Mar. 6, 2018

(86) PCT No.: PCT/EP2018/055509
§ 371 (c)(1),
(2) Date: Sep. 5, 2019

(87) PCT Pub. No.: WO2018/162503
PCT Pub. Date: Sep. 13, 2018

(65) Prior Publication Data
US 2020/0016075 A1    Jan. 16, 2020

(30) Foreign Application Priority Data

Mar. 6, 2017 (EP) .................................... 17159458

(51) Int. Cl.
*A61K 9/08* (2006.01)
*A61K 47/10* (2017.01)
*A61K 47/18* (2017.01)
*A61K 47/20* (2006.01)
*C07K 16/24* (2006.01)

(52) U.S. Cl.
CPC .............. *A61K 9/08* (2013.01); *A61K 47/10* (2013.01); *A61K 47/183* (2013.01); *A61K 47/20* (2013.01); *C07K 16/241* (2013.01)

(58) Field of Classification Search
None
See application file for complete search history.

(56) References Cited

U.S. PATENT DOCUMENTS

| | | | |
|---|---|---|---|
| 8,241,632 B2 | 8/2012 | Rehder et al. | |
| 9,382,317 B2 | 7/2016 | Manning et al. | |
| 2003/0138417 A1 | 4/2003 | Kaisheva et al. | |
| 2004/0033228 A1 | 2/2004 | Krause et al. | |
| 2008/0112953 A1 | 5/2008 | McAuley et al. | |
| 2012/0301460 A1 | 11/2012 | Bao et al. | |
| 2013/0209465 A1 | 8/2013 | Jezek et al. | |
| 2014/0141008 A1* | 5/2014 | Fraunhofer | A61P 29/00 424/142.1 |
| 2020/0016074 A1 | 1/2020 | Badiali et al. | |
| 2020/0023061 A1 | 1/2020 | Jezek et al. | |
| 2020/0023062 A1 | 1/2020 | Jezek et al. | |
| 2020/0069799 A1 | 3/2020 | Jezek et al. | |
| 2020/0071352 A1 | 3/2020 | Jezek et al. | |

FOREIGN PATENT DOCUMENTS

| | | |
|---|---|---|
| EP | 2238985 A1 | 10/2010 |
| EP | 3372241 A1 | 9/2018 |
| EP | 3372242 A1 | 9/2018 |
| WO | WO-9729131 A1 | 8/1997 |
| WO | WO-0187329 A1 | 11/2001 |
| WO | WO-03072060 A2 | 9/2003 |
| WO | 2004/007520 A2 | 1/2004 |
| WO | WO-2006081587 A2 | 8/2006 |
| WO | WO-2006096488 A2 | 9/2006 |
| WO | WO-2007109221 A2 | 9/2007 |
| WO | WO-2008084237 A2 | 7/2008 |
| WO | 2008/157356 A2 | 12/2008 |
| WO | WO-2010062896 A1 | 6/2010 |
| WO | WO-2012013980 A1 | 2/2012 |
| WO | WO-2013011076 A2 | 1/2013 |
| WO | WO-2013114112 A2 | 8/2013 |
| WO | WO-2013164837 A1 | 11/2013 |
| WO | WO-2014039903 A2 | 3/2014 |
| WO | WO-2014114651 A9 | 7/2014 |
| WO | WO-2016066688 A1 | 5/2016 |
| WO | WO-2016103093 A1 | 6/2016 |
| WO | WO 2016/109822 A1 | 7/2016 |

(Continued)

OTHER PUBLICATIONS

Akers, M. J., et al., "Formulation Development of Protein Dosage Forms," Pharmaceutical Biotechnology, 14:47-127 (2002).
Carpenter, J. F., "Rational Design of Stable Lyophilized Protein Formulations: Some Practical Advice," Pharmaceutical Research, 14(8):969-975 (1997).
Vangenende, V., et al., "Mechanisms of Protein Stabilization and Prevention of Protein Aggregation by Glycerol," Biochemistry, 48:11084-11096 (2009).
Wang, W., "Instability, stabilization, and formulation of liquid protein pharmaceuticals," Int'l Journal of Pharmaceutics, 185:129-188 (1999).

(Continued)

*Primary Examiner* — Brian Gangle
(74) *Attorney, Agent, or Firm* — Nixon & Vanderhye P.C.

(57) ABSTRACT

The present invention relates to novel liquid pharmaceutical compositions of adalimumab, which include adalimumab or a biosimilar thereof, arginine and/or methionine, and a small polyol stabiliser such as glycerol. Such a combination of components furnishes formulations having a stability (e.g. on storage and when exposed to stress) which is comparable to or an improvement upon those known in the art, and with fewer ingredients. Such advances will help adalimumab treatments to become more widely available at lower cost, and prolong the viability of pre-loaded delivery devices (e.g. pre-filled syringes) to reduce unnecessary waste of the drug.

23 Claims, No Drawings

(56) References Cited

FOREIGN PATENT DOCUMENTS

| | | |
|---|---|---|
| WO | WO-2016120413 A1 | 8/2016 |
| WO | WO-2016162819 A1 | 10/2016 |
| WO | WO-2018011404 A1 | 1/2018 |
| WO | WO-2018154319 A1 | 8/2018 |
| WO | WO-2018154320 A1 | 8/2018 |
| WO | WO-2018162500 A1 | 9/2018 |
| WO | WO-2018184692 A1 | 10/2018 |
| WO | WO-2018184693 A1 | 10/2018 |

OTHER PUBLICATIONS

Nicoud, L., et al., "Effect of polyol sugars on the stabilization of monoclonal antibodies," Biophys Chem., 197:40-46 (2015).

Mark Cornell Manning et al., "Stability of Protein Pharmaceuticals: An Update", Pharmaceutical Research, vol. 27, No. 4, Apr. 2010, 33 pages.

Daugherty et al., "Formulation and delivery issues for monoclonal antibody therapeutics", Advanced Drug Delivery Reviews, 58:686-706 (2006).

Wang et al., MiniReview, "Antibody Structure, Instability, and Formulation", Journal of Pharmaceutical Sciences, 96(1):1-26 (2007).

\* cited by examiner

LIQUID PHARMACEUTICAL COMPOSITION

CROSS REFERENCE TO RELATED APPLICATIONS

This application is a U.S. National Phase of PCT Application No. PCT/EP2018/055509, filed Mar. 6, 2018, which claims priority to European Patent Application No. 17159458.3, filed Mar. 6, 2017, each of which is incorporated herein by reference.

INTRODUCTION

The present invention relates to a novel protein formulation. In particular, the invention relates to a liquid pharmaceutical composition of adalimumab, to a method of manufacturing the composition, to a kit including the composition, to a package including the composition, to a method of manufacturing the package, and to methods of treatment using the composition and/or package.

BACKGROUND

Treatment of tumour necrosis factor-alpha (TNF-α)-related autoimmune diseases, such as rheumatoid arthritis, psoriasis and other autoimmune diseases, has been achieved through the use of FDA-approved drugs such as Adalimumab (HUMIRA®, Abbott Corporation). Adalimumab is a human monoclonal antibody that inhibits human TNF-α activity so as to prevent it from activating TNF receptors, thereby downregulating inflammatory responses associated with autoimmune diseases. Approved medical indications for Adalimumab include rheumatoid arthritis, psoriatic arthritis, ankylosing spondylitis, Crohn's disease, ulcerative colitis, moderate to severe chronic psoriasis and juvenile idiopathic arthritis.

Adalimumab is generally delivered to a patient via subcutaneous injection, and is thus provided in a liquid form, typically in packages such as vials, preloaded syringes, or preloaded "pen devices". Commercially available pen devices (HUMIRA® Pen) generally include a 1 mL prefilled glass syringe, preloaded with 0.8 mL of a sterile formulation of 40 mg Adalimumab (see below), with a fixed needle (either gray natural rubber or a latex free version) and a needle cover. Commercial formulations (HUMIRA®) of Adalimumab contain the following ingredients:

| Ingredient | Amount per container (mg) (filling volume = 0.8 mL) | Amount (mg/mL) |
|---|---|---|
| Adalimumab | 40 | 50 |
| Citric Acid Monohydrate | 1.04 | 1.3 |
| Dibasic sodium phosphate dihydrate | 1.22 | 1.53 |
| Mannitol | 9.6 | 12 |
| Monobasic sodium phosphate dihydrate | 0.69 | 0.86 |
| Polysorbate 80 | 0.8 | 1 |
| Sodium chloride | 4.93 | 6.16 |
| Sodium citrate | 0.24 | 0.3 |
| WFI and sodium hydroxide | q.b. to adjust pH to 5.2 | q.b. to adjust pH to 5.2 |

Moreover, a prefilled syringe or pen which provides either 40 mg/0.4 mL or 80 mg/80 mL (i.e. 100 mg/mL) of Adalimumab has recently been commercialised. The formulations contain the following ingredients:

| Ingredient | 40 mg/0.4 mL Amount per 0.4 mL | 80 mg/80 mL Amount per 0.8 mL |
|---|---|---|
| Adalimumab | 40 mg | 80 mg |
| Mannitol | 16.8 mg | 33.6 mg |
| Polysorbate 80 | 0.4 mg | 0.8 mg |
| Water for injection USP | q.s. | q.s. |

Adalimumab, and its method of manufacture, is described in WO97/29131 (BASF) as D2E7, and elsewhere in the art.

Though the aforementioned commercial formulation of Adalimumab is stable (at least to some extent), the relevant antibody may be unstable over prolonged periods or under stressed conditions, thus precluding prolonged storage of said formulations. Such degradation of the formulation may be due to a variety of factors, including:

Physical effects, such as:
Inadequate inhibition of aggregation of the relevant protein molecules (a function supposedly served by Tween 80, particularly if aggregation occurs at the liquid/air interface);
Inadequate inhibition of precipitation;
Inadequate inhibition of adsorption of the relevant protein molecules at the interface of water and air or at the contact surface of any packaging material (a function supposedly served by Tween 80);
Inadequate inhibition of protein unfolding;
Inadequate regulation of osmotic pressure (a function supposedly served by mannitol);
Chemical effects, such as:
Inadequate regulation of oxidation (a function supposedly served by mannitol and potentially undermined by Tween 80, which can promote oxidation of double bonds);
Inadequate inhibition of photo-oxidation;
Inadequate inhibition of hydrolysis of ester bonds leading to the formation of acid, aldehyde and peroxide products, thus affecting the stability of the antibody;
Inadequate stabilisation and maintenance of pH;
Inadequate inhibition of protein fragmentation;
Inadequate inhibition of deamidation, cyclic imide formation or isomerisation.

Any, some, or all of the above factors can lead to either an unviable drug product (which may be unsafe for use in medical treatments) or a drug product whose viability is variable and unpredictable, especially in view of the variable stresses (agitation, heat, light) different batches of drug product may be exposed to during manufacture, transport, and storage.

In terms of the physical and chemical stabilisation of Adalimumab, the complex array of components within the aforementioned commercial formulations appears to perform below expectations, especially in view of the large number of components. Though this particular combination of excipients undoubtably represents a 'delicate balance' (given the interplay between various technical factors) and was the result of extensive research and development, in view of the risk of underperformance it is questionable whether such a large number of different excipients is justified, especially given that this inevitably increases processing and cost burdens, toxicity risks, and risks of deleterious interactions between components that could compromise the formulation. Even if the overall performance of the commercial formulations could not be surpassed, an alternative formulation having comparative performance but containing few components would represent a highly desirable replacement for the commercial formulations, for at least the aforesaid reasons.

In order to guarantee reproducible clinical performance of a protein-based pharmaceutical product, such products must remain in a stable and consistent form over time. It is well-established that molecular alterations can occur during every stage of the manufacturing process, including during the production of the final formulation and during storage. Molecular alterations can modify a quality attribute of a biopharmaceutical product, resulting in an undesirable change in the identity, strength or purity of the product. Some such problems are outlined above.

The primary goal of formulation development is to provide a pharmaceutical composition that will support the stability of a biopharmaceutical protein during all stages of its production, storage, shipping and use. Another goal for formulations that are meant for subcutaneous administration is to reduce injection pain. Formulation development for an innovative biopharmaceutical protein, or a biosimilar monoclonal antibody (mAb), is essential to its safety, clinical efficacy and commercial success.

There is therefore a need for the provision of alternative or improved liquid formulations of adalimumab. Desirably, any new formulations would solve at least one of the aforementioned problems and/or at least one problem inherent in the prior art, and may suitably solve two or more of said problems. Desirably, the problem(s) of the prior art may be solved whilst reducing the complexity of the formulation.

SUMMARY OF THE INVENTION

During extensive research into the complex area of antibody formulations, the present inventors realised that liquid formulations, of adalimumab in particular, could be stabilized by the addition of either arginine or methionine. Since individual amino acids tend to interact with a given protein molecule in their own unique manner (be it stabilizing or destabilizing to the given protein), predicting stabilizing or destabilizing effects of combinations of amino acids can be extremely difficult, even where the effects of individual amino acids of the combination are known. It was therefore surprising to the present inventors that the addition of a combination of both arginine and methionine to adalimumab formulations imparts a significant stabilizing effect, suggesting an unpredictable positive synergy between the two amino acids in this particular context. The inventors were further surprised to discover the adalimumab formulation stability could be yet further increased through inclusion of a small polyol, e.g., a polyol having 2 to 6 carbon atoms, such as glycerol.

The formulations of the invention are stable even at high concentrations of adalimumab (e.g., 100 mg/ml). Therefore, the new formulations permit administration of high amounts (e.g., effective amounts) of antibody in smaller volumes as compared to the aforementioned commercial adalimumab formulation, thereby decreasing pain.

In particular, the present invention provides the following embodiments:

1. A liquid pharmaceutical composition comprising:
   (a) adalimumab;
   (b) arginine;
   wherein the composition further comprises either or both methionine and/or a polyol; wherein the polyol is a C2-C6 polyol, suitably comprising at most five hydroxyl groups, suitably 2-3 hydroxyl groups.

2. A liquid pharmaceutical composition comprising:
   (a) adalimumab;
   (b) methionine;
   wherein the composition further comprises either or both arginine and/or a polyol; wherein the polyol is a C2-C6 polyol, suitably comprising at most five hydroxyl groups, suitably 2-3 hydroxyl groups.

3. A liquid pharmaceutical composition comprising:
   (a) adalimumab;
   (b) a polyol;
   wherein the composition further comprises either or both methionine and/or arginine; wherein the polyol is a C2-C6 polyol, suitably comprising at most five hydroxyl groups, suitably 2-3 hydroxyl groups.

4. A liquid pharmaceutical composition comprising:
   (a) adalimumab;
   (b) arginine;
   (c) methionine; and
   (d) a C2-C6 polyol.

5. The liquid pharmaceutical composition according to item 4, wherein the polyol is a C2-C4 polyol.

6. The liquid pharmaceutical composition according to item 5, wherein the C2-C4 polyol is glycerol.

7. The liquid pharmaceutical composition according to any one of items 1 to 6, wherein the composition further comprises a buffer system.

8. The liquid pharmaceutical composition according to item 7, wherein the buffer system is an acetate buffer system.

9. The liquid pharmaceutical composition according to any one of items 1 to 8, comprising 25 to 125 mg/ml adalimumab.

10. The liquid pharmaceutical composition according to item 4 comprising:
    (a) adalimumab;
    (b) arginine;
    (c) methionine;
    (d) a C2-C6 polyol;
    (e) a buffer system;
    (f) a surfactant; and
    (g) optionally a tonicifier;
    wherein the composition has a pH between 4.0 and 6.0.

11. The liquid pharmaceutical composition according to item 10 comprising:
    (a) adalimumab;
    (b) arginine;
    (c) methionine;
    (d) a C2-C4 polyol;
    (e) an acetate buffer system;
    (f) a non-ionic surfactant; and
    (g) optionally sodium chloride (though suitably at most 40 mM thereof);
    wherein the composition has a pH between 4.8 and 5.4.

12. The liquid pharmaceutical composition according to item 11 comprising, consisting essentially of, or consisting of:
    (a) 25-125 mg/ml adalimumab;
    (b) 50-70 mM L-arginine;
    (c) 20-40 mM L-methionine;
    (d) 100-150 mM glycerol and/or propylene glycol;
    (e) 5-10 mM (sodium) acetate buffer;
    (f) 20-40 mM sodium chloride; and
    (g) 0.5-2 mg/ml polysorbate 20 or poloxamer 188;
    wherein the composition has a pH between 4.8 and 5.3.

13. The liquid pharmaceutical composition according to item 12 comprising, consisting essentially of, or consisting of:

(a) 100 mg/ml adalimumab;
(b) 60 mM L-arginine;
(c) 30 mM L-methionine;
(d) 130 mM glycerol and/or propylene glycol;
(e) 8 mM (sodium) acetate buffer;
(f) 30 mM sodium chloride; and
(g) 1 mg/ml polysorbate 20 or poloxamer 188;
wherein the composition has a pH of 5.0 (optionally +/−0.5).
14. The liquid pharmaceutical composition according to item 11 comprising, consisting essentially of, or consisting of:
(a) 25-125 mg/ml adalimumab;
(b) 50-70 mM L-arginine;
(c) 20-40 mM L-methionine;
(d) 100-150 mM glycerol and/or propylene glycol;
(e) 5-10 mM (sodium) acetate buffer; and
(f) 0.5-2 mg/ml polysorbate 20 or poloxamer 188;
wherein the composition has a pH between 4.9 and 5.4.
15. The liquid pharmaceutical composition according to item 14 comprising, consisting essentially of, or consisting of:
(a) 100 mg/ml adalimumab;
(b) 60 mM L-arginine;
(c) 30 mM L-methionine;
(d) 130 mM glycerol and/or propylene glycol;
(e) 8 mM (sodium) acetate buffer; and
(f) 1 mg/ml polysorbate 20 or poloxamer 188;
wherein the composition has a pH of 5.2 (optionally +/−0.2).
16. A drug delivery device comprising a liquid pharmaceutical composition as defined in any preceding item.
17. A liquid pharmaceutical composition as defined in any of items 1 to 15 for use in in the treatment of a disease or disorder.
18. A liquid pharmaceutical composition as defined in any of items 1 to 15 for use in the treatment of rheumatoid arthritis, psoriatic arthritis, ankylosing spondylitis, Crohn's disease, ulcerative colitis, psoriasis, hidradenitis suppurative, uveitis and/or juvenile idiopathic arthritis.
19. A method of manufacturing a liquid pharmaceutical composition, the method comprising mixing together adalimumab, arginine, methionine and a C2-C6 polyol.
20. A solid composition obtainable by freeze-drying a liquid pharmaceutical composition as defined in any of items 1 to 15.
21. The liquid pharmaceutical composition according to item 14 or 15, wherein the composition is free of, substantially free of, or comprises at most 40 mM of a tonicifier.

Any features, including optional, suitable, and preferred features, described in relation to any particular aspect of the invention may also be features, including optional, suitable and preferred features, of any other aspect of the present invention.

DETAILED DESCRIPTION OF THE INVENTION

Definitions

Unless otherwise stated, the following terms used in the specification and claims have the following meanings set out below.

References herein to "adalimumab" include the originator drug substance (as commercially available), adalimumab as defined in WO97/29131 (BASF) (particularly D2E7 therein) and elsewhere in the art, and also biosimilars thereof. D2E7 of WO97/29131 "has a light chain CDR3 domain comprising the amino acid sequence of SEQ ID NO: 3 and a heavy chain CDR3 domain comprising the amino acid sequence of SEQ ID NO: 4". Preferably, the D2E7 antibody has a light chain variable region (LCVR) comprising the amino acid sequence of SEQ ID NO: 1 and a heavy chain variable region (HCVR) comprising the amino acid sequence of SEQ ID NO: 2. WO97/29131 gives details of each of these sequence listings. References herein to "adalimumab" may include biosimilars which, for instance, may share at least 75%, suitably at least 80%, suitably at least 85%, suitably at least 90%, suitably at least 95%, suitably at least 96%, suitably at least 97%, suitably at least 98% or most suitably at least 99% protein sequence identity with any one of protein sequences disclosed in either WO97/29131 (especially in relation to D2E7) or elsewhere in relation to "adalimumab". Alternatively or additionally, references herein to "adalimumab" may include biosimilars which exhibit at least 75%, suitably at least 80%, suitably at least 85%, suitably at least 90%, suitably at least 95%, suitably at least 96%, suitably at least 97%, suitably at least 98% or most suitably at least 99% protein sequence homology with any one of protein sequences disclosed in either WO97/29131 (especially in relation to D2E7) or elsewhere in relation to "adalimumab". Alternatively or additionally, a biosimilar may have a (slightly) different glycosylation profile, even if the protein sequence is substantially the same or different to the extent specified above.

The term "biosimilar" (also known as follow-on biologics) is well known in the art, and the skilled person would readily appreciate when a drug substance would be considered a biosimilar of adalimumab. Furthermore, such "biosimilars" would need to be officially approved as a "biosimilar" for marketing before said "biosimilar" is sold on the open market. The term "biosimilar" is generally used to describe subsequent versions (generally from a different source) of "innovator biopharmaceutical products" ("biologics" whose drug substance is made by a living organism or derived from a living organism or through recombinant DNA or controlled gene expression methodologies) that have been previously officially granted marketing authorisation. Since biologics have a high degree of molecular complexity, and are generally sensitive to changes in manufacturing processes (e.g. if different cell lines are used in their production), and since subsequent follow-on manufacturers generally do not have access to the originator's molecular clone, cell bank, know-how regarding the fermentation and purification process, nor to the active drug substance itself (only the innovator's commercialized drug product), any "biosimilar" is unlikely to be exactly the same as the innovator drug product.

For the purposes of various molar calculations (e.g. for molar ratios between adalimumab and another component of the liquid pharmaceutical composition of the invention) the molecular weight of adalimumab may be taken to be 144190.3 g/mol (reference molecular weight) based on details disclosed on the CAS database for CAS #331731-18-1, Adalimumab, where the molecular formula is taken as $C_{6428}H_{9912}N_{1694}O_{1987}S_{46}$. As such, a liquid pharmaceutical composition containing 50 mg/mL adalimumab may be considered a 0.347 mM (or 347 μM) solution of adalimumab. This is not intended to be in any way limiting regarding the nature of any biosimilars of adalimumab covered by the scope of the present invention, nor the level of glycosylation, either of which may effect the actual molecular weight. However, where a biosimilar does have a different molecular weight, the abovementioned reference molecular weight should be suitably used for the purposes of assessing whether or not such a biosimilar falls within the scope of any molar definitions stipulated within this specification. So the number of moles in a known weight of said biosimilar should be calculated, just for the purposes of this invention, using the above reference molecular weight.

Herein, the term "buffer" or "buffer solution" refers to a generally aqueous solution comprising a mixture of an acid (usually a weak acid, e.g. acetic acid, citric acid, imidazolium form of histidine) and its conjugate base (e.g. an acetate or citrate salt, for example, sodium acetate, sodium citrate, or histidine) or alternatively a mixture of a base (usually a weak base, e.g. histidine) and its conjugate acid (e.g. protonated histidine salt). The pH of a "buffer solution" will change very only slightly upon addition of a small quantity of strong acid or base due to the "buffering effect" imparted by the "buffering agent".

Herein, a "buffer system" comprises one or more buffering agent(s) and/or an acid/base conjugate(s) thereof, and more suitably comprises one or more buffering agent(s) and an acid/base conjugate(s) thereof, and most suitably comprises one buffering agent only and an acid/base conjugate thereof. Unless stated otherwise, any concentrations stipulated herein in relation to a "buffer system" (i.e. a buffer concentration) suitably refers to the combined concentration of the buffering agent(s) and/or acid/base conjugate(s) thereof. In other words, concentrations stipulated herein in relation to a "buffer system" suitably refer to the combined concentration of all the relevant buffering species (i.e. the species in dynamic equilibrium with one another, e.g. acetate/acetic acid). As such, a given concentration of an acetate buffer system generally relates to the combined concentration of acetate (or acetate salt(s), e.g. sodium acetate) and acetic acid. The overall pH of the composition comprising the relevant buffer system is generally a reflection of the equilibrium concentration of each of the relevant buffering species (i.e. the balance of buffering agent(s) to acid/base conjugate(s) thereof).

Herein, the term "buffering agent" refers to an acid or base component (usually a weak acid or weak base) of a buffer or buffer solution. A buffering agent helps maintain the pH of a given solution at or near to a pre-determined value, and the buffering agents are generally chosen to complement the pre-determined value. A buffering agent is suitably a single compound which gives rise to a desired buffering effect, especially when said buffering agent is mixed with (and suitably capable of proton exchange with) an appropriate amount (depending on the pre-determined pH desired) of its corresponding "acid/base conjugate", or if the required amount of its corresponding "acid/base conjugate" is formed in situ—this may be achieved by adding strong acid or base until the required pH is reached. By way of example:

An acetate "buffering agent" is suitably an acetate salt, for example, sodium acetate, suitably mixed with its acid/base conjugate, acetic acid. Such a buffer system may be formed by simply mixing a given amount of sodium acetate with a given amount of acetic acid (or indeed another acid, e.g. HCl). Alternatively, however, such a buffer may be formed by adding a given amount of a base, suitably a strong base (e.g. sodium hydroxide) to the acetic acid until the desired pH (and thus the desired balance of sodium acetate/acetic acid) is reached. Herein, except where the contrary is stated, any concentrations given in relation to an acetate buffer or acetate buffering agent suitably refer to the combined concentration of the buffering agent(s) (e.g. sodium acetate) and/or acid/base conjugate(s) thereof (e.g. acetic acid). The skilled person is readily able to calculate such concentrations. Such concentrations may be calculated by reference to the combined concentrations of buffering agent(s) and acid/base conjugate(s), where a buffer system is formed by simply mixing together buffering agent(s) and acid/base conjugate(s). Alternatively, where a buffer system is formed by mixing either the buffering agent(s) or acid/base conjugate(s) with a pH adjuster (e.g. strong acid or strong base) to produce a mixture of each, suitably such concentrations may be calculated by reference to the starting amounts/concentrations of the buffering agent(s) or acid/base conjugate(s) respectively. For example, where a buffer system is formed using a known amount/concentration of acetic acid which is mixed with a pH adjuster (e.g. sodium hydroxide) until the desired pH is reached, the concentration of the buffer system may be calculated by reference to the initial amount of acetic acid.

Herein, an "acid/base conjugate" refers to the conjugate acid or conjugate base (whichever is relevant at a particular pH—typically the conjugate acid in the context of the present invention) of a particular "buffering agent". The acid/base conjugate of an acetate buffering agent (e.g. sodium acetate) is suitably acetic acid.

Herein, the term "buffering species" refers to the particular species (excluding any associated counteranions or countercations—i.e. ignore sodium ions for sodium acetate/acetic acid systems) of a given buffer system which are in dynamic equilibrium with (and proton-exchange with) one another. For example, acetate anions and acetic acid together constitute the "acetate buffering species" of a "acetate buffer system".

Since it is somewhat difficult to define quantities (whether absolute or relative) of a buffer system by reference to weight (since the total weight will depend on the desired pH, which will affect the amount of counterions present), herein weight-based quantities may instead be determined by reference to a theoretical weight of the relevant "buffering species". At least two species are present in any given set of "buffering species" (in relative amounts that can only be determined by reference to the pH), each with a different molecular weight (which usually differs by just 1). Therefore, to enable viable weight calculations and references, for the purposes of this specification the weight of any given set of "buffering species" is given as a theoretical weight based on just one of the buffering species, namely the most acidic of the buffering species (i.e. the most protonated form at any given pH). So the weight of a given set of "buffering species" is quoted as the weight of acid-species equivalents. By way of example, in an acetate buffer system the acetate buffering species may consist of acetate anions (ignore countercations) and acetic acid. The weight of the "buffering species" is therefore calculated as if acetic acid was the only species present in the buffer system (even though acetate is clearly present alongside acetic acid). Thus, any reference to a weight or weight ratio involving a "acetate buffering species" suitably refers to the theoretical weight of acetic acid equivalents within the buffer system. As such, where a composition is formed by adding a pH adjuster (e.g. sodium hydroxide) to a fixed amount of acetic acid, the original weight of acetic acid may be considered to be the weight of the "buffering species" regardless of the ultimate pH. Alternatively, if the concentration (i.e. molarity) of a buffer system is known, this can be converted into a weight of "buffering species" by reference to the molecular weight of the most acidic form of the relevant buffering species (e.g. acetic acid), and ignoring the fact that acetate anions are also present.

Unless stated otherwise, references herein to an "amino acid" or "amino acids", whether specific (e.g. arginine, histidine) or general (e.g. any amino acid), in the context of their presence or otherwise within compositions (especially pharmaceutical liquid compositions of the invention) relate to the corresponding free amino acid(s) (regardless of its/their protonation state and/or salt form, though for consistency amounts are suitably calculated by reference to the free amino acid per se). This may suitably include natural and/or artificial amino acids. Unless stated to the contrary, such references are not intended to relate to amino acid residue(s) covalently incorporated as part of a larger compound (as opposed to a composition comprising multiple compounds), such as a peptide or protein (where such amino acid residues are linked via peptide bonds). As such, though adalimumab, as a protein, contains amino acid residues, it is not considered to comprise any "free amino acid(s)". By way of example, a composition defined as being "free of arginine" does not contain any free arginine but it may still include one or more proteins (e.g. adalimumab) which do themselves comprise arginine residues.

Unless stated otherwise, references herein to any one or more "amino acids", whether specific or general, suitably relate to the L-stereoisomers or a racemate thereof, most suitably L-amino acids.

Herein, in the context of the present specification, a "strong acid" is suitably one having a $pK_a$ of −1.0 or less, whereas a "weak acid" is suitably one having a $pK_a$ of 2.0 or more. Herein, in the context of the present specification, a "strong base" is suitably one whose conjugate acid has a $pK_a$ of 12 or higher (suitably 14 or higher), whereas a "weak base" is suitably one whose conjugate acid has a $pK_a$ of 10 or less.

Herein, a "stabiliser" refers to a component which facilitates maintenance of the structural integrity of the biopharmaceutical drug, particularly during freezing and/or lyophilization and/or storage (especially when exposed to stress). This stabilising effect may arise for a variety of reasons, though typically such stabilisers may act as osmolytes which mitigate against protein denaturation. Typical stabilisers include amino acids (i.e. free amino acids not part of a peptide or protein—e.g. glycine, arginine, histidine, aspartic acid, lysine) and sugar stabilisers, such as a sugar polyol (e.g. mannitol, sorbitol), though the liquid pharmaceutical compositions of the invention include methionine, arginine and a C2-C6 polyol as stabilisers.

Herein, a "polyol" is a substance with multiple hydroxyl groups, and includes sugars (reducing and nonreducing sugars), sugar alcohols and sugar acids. Suitably, the polyol is a sugar alcohol.

Herein, the type, size, and/or nature of any given "polyol" may be defined by reference to a number of carbon atoms contained within the molecular structure of the polyol. As such, generic references to a C[x]-C[y] polyol (or analogously to a (x-yC) polyol)) are suitably references to a polyol containing between x and y carbon atoms. By way of example, a C2-C3 polyols would suitably include ethylene glycol (C2), propylene glycol (C3), and glycerol (C3). A C6 polyol may suitably include mannitol. The number and arrangements of other atoms, such as hydrogen and oxygen atoms, are not necessarily constrained in any specific manner by the stipulated carbon chain length. In addition to specifying a number of carbon atoms contained within a given polyol, a polyol may be defined by reference to the number of hydroxyl groups. For instance, a C2-C3 polyol comprising three hydroxyl groups suitably includes glycerol (which has three hydroxyl groups) but excludes ethylene glycol and propylene glycol (each of which have only two hydroxyl groups). A polyol may also be defined generically by reference to a maximum number of hydroxyl groups. For instance, a C2-C6 polyol comprising at most 5 hydroxyl groups is by definition a polyol having between 2 and 5 hydroxyl groups.

Herein, a "non-reducing sugar" is generally a sugar without any aldehyde moieties or without the capability of forming an aldehyde moiety (e.g. through isomerism).

Herein, a "tonicity modifier" or "tonicifier" refers to a reagent whose inclusion within a composition suitably contributes to (or increases) the overall osmolality and osmolarity of the composition. Suitably, a tonicifier, as used herein includes an agent which functions to render a solution similar in osmotic characteristics to physiologic fluids.

Herein, references to specific amounts of a given component of a composition, especially a buffering agent, stabiliser, amino acid, surfactant, or tonicifier, suitably relate to the amounts of the pure anhydrous form of the relevant component (or compositions formed by using said amounts of the pure anhydrous form), even though such a component may be used in a non-anhydrous form when forming the composition. Amounts of any corresponding non-anhydrous forms (e.g. monohydrates, dihydrates, etc.) may be readily calculated by simply using the appropriate multiplier. For instance, unless stated otherwise (as per the Examples, where quantities relate to trehalose dihydrate), amounts stipulated in relation to trehalose refer to the anhydrous form of trehalose (or compositions formed by using the stipulated amounts/concentrations of anhydrous trehalose), which has a molecular weight of 342.296 g/mol, so to calculate the corresponding amount of trehalose dihydrate needed to form the same composition (less water would have to be added) it is necessary to multiply the stipulated amount by 378.33/342.296, since 378.33 is the molecular weight of trehalose dihydrate. The skilled person would readily understand how to judiciously adjust the quantity of diluent/water depending on the form of the components used, in order to derive the target concentrations.

Herein, the term "pharmaceutical composition" refers to a formulation of a pharmaceutical active which renders the biological activity of the active ingredient therapeutically effective, but which does not include other ingredients which are obviously toxic to a subject to which the formulation are intended to be administered.

Herein, the term "stable" generally refers to the physical stability and/or chemical stability and/or biological stability of a component, typically an active or composition thereof, during preservation/storage.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

In the context of the present invention, a "therapeutically effective amount" or "effective amount" of the antibody means an amount that is effective, when administered to a mammal for treating a disease or disorder, in prophylactic and therapeutic aspect and the antibody is effective in treatment of the diseases concerned.

The "therapeutically effective amount" will vary depending on the compound, the disease and its severity and the age, weight, etc., of the mammal to be treated.

The term "human TNF-α" refers to the human cytokine which exists in a 17 kD secreted form and a 26 kD membrane-associated form, and in a biologically active form, TNF-α could be observed as a trimer of covalently-bound 17 kD molecule. Its specific structure can be found in Pennica, D. et al. (1984) Nature 312: 724-729; Davis, J. M. et al. (1987) Biochemistry 26, 1322-1326; and Jones, E. Y. et al. (1989) Nature 338: 225-228.

The term "recombinant human antibody" is intended to include a human antibody prepared, expressed, produced or isolated using a recombinant method.

Herein, amounts stipulated for components and ingredients, whether specified in terms of "parts", ppm (parts per million), percentages (%, e.g. wt %), or ratios, are intended to be by weight, unless stated otherwise.

Where the quantity or concentration of a particular component of a given composition is specified as a weight percentage (wt % or %w/w), said weight percentage refers to the percentage of said component by weight relative to the total weight of the composition as a whole. It will be understood by those skilled in the art that the sum of weight percentages of all components of a composition (whether or not specified) will total 100 wt %. However, where not all components are listed (e.g. where compositions are said to "comprise" one or more particular components), the weight percentage balance may optionally be made up to 100 wt % by unspecified ingredients (e.g. a diluent, such as water, or other non-essential but suitable additives).

Herein, unless stated otherwise, the term "parts" (e.g. parts by weight, pbw) when used in relation to multiple ingredients/components, refers to relative ratios between said multiple ingredients/components. Expressing molar or weight ratios of two, three or more components gives rise to the same effect (e.g. a molar ratio of x, y, and z is x1:y1:z1 respectively, or a range x1-x2:y1-y2:z1-z2). Though in many embodiments the amounts of individual components within a composition may be given as a "wt %" value, in alternative embodiments any or all such wt % values may be converted to parts by weight (or relative ratios) to define a multi-component composition. This is so because the relative ratios between components is often more important than the absolute concentrations thereof in the liquid pharmaceutical compositions of the invention. Where a composition comprising multiple ingredients is described in terms of parts by weight alone (i.e. to indicate only relative ratios of ingredients), it is not necessary to stipulate the absolute amounts or concentrations of said ingredients (whether in toto or individually) because the advantages of the invention can stem from the relative ratios of the respective ingredients rather than their absolute quantities or concentrations. However, in certain embodiments, such compositions consists essentially of or consist of the stipulated ingredients and a diluents (e.g. water).

Where a composition is said to comprise a plurality of stipulated ingredients (optionally in stipulated amounts of concentrations), said composition may optionally include additional ingredients other than those stipulated. However, in certain embodiments, a composition said to comprise a plurality of stipulated ingredients may in fact consist essentially of or consist of all the stipulated ingredients.

Herein, where a composition is said to "consists essentially of" a particular component, said composition suitably comprises at least 70 wt % of said component, suitably at least 90 wt % thereof, suitably at least 95 wt % thereof, most suitably at least 99 wt % thereof. Suitably, a composition said to "consist essentially of" a particular component consists of said component save for one or more trace impurities.

Suitably, unless stated otherwise, where reference is made to a parameter (e.g. pH, pKa, etc.) or state of a material (e.g. liquid, gas, etc.) which may depend on pressure and/or temperature, suitably in the absence of further clarification such a reference refers to said parameter at standard ambient temperature and pressure (SATP). SATP is a temperature of 298.15 K (25° C., 77° F.) and an absolute pressure of 100 kPa (14.504 psi, 0.987 atm). References herein to "standard pressure" suitably refer to an absolute pressure of about 100 kPa.

The term "substantially free", when used in relation to a given component of a composition (e.g. "a liquid pharmaceutical composition substantially free of compound X"), refers to a composition to which essentially none of said component has been added. When a composition is "substantially free" of a given component, said composition suitably comprises no more than 0.01 wt % of said component, suitably no more than 0.001 wt % of said component, suitably no more than 0.0001 wt %, suitably no more than 0.00001 wt %, suitably no more than 0.000001 wt % thereof, most suitably no more than 0.0001 parts per billion (by weight).

Herein, unless stated otherwise, all chemical nomenclature may be defined in accordance with IUPAC definitions.

Liquid Pharmaceutical Composition

The present invention provides a liquid pharmaceutical composition, suitably as defined herein. The composition suitably comprises adalimumab, which in itself suitably includes any biosimilar thereof. The composition suitably comprises arginine, methionine and a C2-C6 polyol, more suitably a C2-C4 polyol. In addition, the composition may suitably include any one or more additional components defined herein in relation to a liquid pharmaceutical composition (e.g. including a buffer, surfactant and tonicifier), optionally in any amount, concentration, or form stipulated herein; and wherein the composition optionally exhibits any one or more parameters or properties given herein in relation to a liquid pharmaceutical composition (e.g. pH, osmolality).

Advantageously, the present invention provides alternative and improved liquid pharmaceutical compositions, which are highly stable even at high adalimumab concentrations and therefore cause little pain upon injection. As is illustrated herein (see Examples), the liquid pharmaceutical formulations of the present invention have comparable or improved characteristics when compared to the conventional formulations of adalimumab, for example the aforementioned commercially available formulation Humira®, when subjected to different stressing conditions (thermal, mechanical and light). Their performance is also generally comparable or better than many other comparative formulations that were subjected to the same stress testing. Since these stressing conditions are highly representative of the kind of stress such formulations are subjected to during manufacture, transport, and storage, they provide an excellent indication of the advantages of the invention. That such good stability performance can be achieved using less complex formulations with fewer excipients was considered surprising in view of the general teachings of the prior art.

Adalimumab

Adalimumab, which is commercially available in HUMIRA® formulations, and its method of manufacture, is described in WO97/29131 (BASF) as D2E7, and elsewhere in the art. It is described as having "a light chain CDR3 domain comprising the amino acid sequence of SEQ ID NO: 3 and a heavy chain CDR3 domain comprising the amino acid sequence of SEQ ID NO: 4" (WO97/29131). Furthermore, the D2E7 antibody is described as having a light chain variable region (LCVR) comprising the amino acid sequence of SEQ ID NO: 1 and a heavy chain variable region (HCVR) comprising the amino acid sequence of SEQ ID NO: 2 (WO97/29131).

The medical indications and function of Adalimumab, are elucidated hereinbefore.

In the context of the invention "adalimumab" includes biosimilars, as defined hereinbefore, and the skilled person would readily appreciate the scope of the term "adalimumab" in the context of the invention.

In an embodiment, the liquid pharmaceutical composition comprises adalimumab at a concentration of from about 5 to about 200 mg/ml, suitably from about 25 to about 125 mg/mL. For example, the adalimumab may be present in the formulation at a concentration of about 25, about 50, about 75 or about 100 mg/ml. In an embodiment, the adalimumab is present at a concentration from about 75 to 125 mg/mL, suitably from about 90 to 110 mg/mL, suitably from about 95 to about 105 mg/ml, and most suitably in an amount of 100 mg/ml. Due to the increased concentration in this embodiment as compared to the aforementioned commercial adalimumab formulation, the same effective amounts can be subcutaneously injected in smaller volumes, thereby decreasing pain of the patients.

Amino Acids

Suitably, the liquid pharmaceutical composition comprises methionine and arginine, most suitably L-methionine and L-arginine. Suitably, such a combination of components facilitates maintenance of the structural integrity of the biopharmaceutical drug, particularly during freezing and/or lyophilization and/or storage (especially when exposed to stress).

It was surprisingly found that methionine and arginine act synergistically to provide a stabilizing effect on adalimumab formulations. This stabilizing effect is even increased when both amino acids are combined in a single adalimumab formulation and even further increased if a C2-C6 polyol is additionally added.

Suitably, the liquid pharmaceutical composition comprises arginine (most suitably L-arginine) at a concentration of from about 5 to about 200 mM, more suitably from about 20 to about 100 mM, more suitably from about 50 to about 70 mM. In an embodiment, L-arginine is present at a concentration of 60 mM.

Suitably, the liquid pharmaceutical composition comprises arginine (most suitably L-arginine) at a concentration of from about 0.5 mg/mL to about 100 mg/mL, more suitably from about 1 mg/mL to about 50 mg/mL, more suitably from about 5 mg/mL to about 15 mg/mL. In an embodiment, arginine is present at a concentration of between 9 mg/mL and 11 mg/mL. In a particular embodiment, L-arginine is present at a concentration of 10.4 mg/mL.

Suitably, the liquid pharmaceutical composition comprises arginine (most suitably L-arginine) in a molar ratio of arginine to adalimumab of from about 1:1 to about 500:1, more suitably from about 10:1 to about 200:1, more suitably from about 50:1 to about 125:1. In an embodiment, arginine is present at a molar ratio of arginine to adalimumab of from about 75:1 to about 100:1, most suitably about 86:1. In an embodiment, L-arginine is present at a molar ratio of L-arginine to adalimumab of about 86:1.

Suitably, the liquid pharmaceutical composition comprises methionine (most suitably L-methionine) at a concentration of from about 1 to about 200 mM, more suitably from about 10 to about 100 mM, more suitably from about 20 to about 40 mM. In an embodiment, L-methionine is present at a concentration of 30 mM.

Suitably, the liquid pharmaceutical composition comprises methionine (most suitably L-methionine) at a concentration of from about 0.5 mg/mL to about 100 mg/mL, more suitably from about 1 mg/mL to about 50 mg/mL, more suitably from about 2.5 mg/mL to about 7.5 mg/mL. In an embodiment, methionine is present at a concentration of between 4 mg/mL and 5 mg/mL. In a particular embodiment, L-methionine is present at a concentration of 4.5 mg/mL.

Suitably, the liquid pharmaceutical composition comprises methionine (most suitably L-methionine) in a molar ratio of methionine to adalimumab of from about 1:1 to about 500:1, more suitably from about 10:1 to about 200:1. In an embodiment, methionine is present at a molar ratio of methionine to adalimumab of from about 30:1 to about 50:1, most suitably about 43:1. In an embodiment, L-methionine is present at a molar ratio of L-methionine to adalimumab of about 43:1.

Suitably, the liquid pharmaceutical composition comprises arginine (most suitably L-arginine) and methionine (most suitably L-methionine) in a respective molar ratio of from about 1:10 to about 10:1, suitably from about 1:5 to about 5:1, suitably from about 1:1 to about 3:1, most suitably about 2:1. Suitably, the molar concentration of arginine is greater than the molar concentration of methionine.

Suitably, the liquid pharmaceutical composition comprises an amino acid combination of arginine and methionine, wherein the molar ratio of the amino acid combination (i.e. the sum of both amino acids combined) to adalimumab is from about 10:1 to about 300:1, suitably from about 50:1 to about 200:1, suitably from about 100:1 to about 150:1, suitably about 130:1.

Suitably, the weight ratio of adalimumab to arginine within the liquid pharmaceutical composition is between 100:1 and 1:1, suitably between 50:1 and 2:1, more suitably between 20:1 and 3:1, more suitably between 15:1 and 5:1, most suitably about 10:1.

Suitably, the weight ratio of adalimumab to methionine within the liquid pharmaceutical composition is between 200:1 and 1:1, suitably between 100:1 and 2:1, more suitably between 50:1 and 5:1, more suitably between 30:1 and 10:1, most suitably about 22:1.

Suitably, the weight ratio of adalimumab to an amino acid combination or arginine and methionine (i.e. combined weights of arginine and methionine) within the liquid pharmaceutical composition is between 100:1 and 1:1, suitably between 50:1 and 2:1, more suitably between 30:1 and 3:1, more suitably between 10:1 and 4:1, most suitably about 7:1.

As illustrated in the Example section, liquid pharmaceutical compositions of the invention including the amino acids as defined herein perform particularly well in stress tests, especially in relation to aggregation, fragmentation and protein unfolding, which can be important indicators of stability and drug product viability. Furthermore, liquid pharmaceutical compositions comprising methionine and arginine, particularly in an amount range as stipulated, perform particularly well.

Polyol Stabiliser

Suitably, the liquid pharmaceutical composition comprises a stabiliser, most suitably a polyol stabiliser. Suitably, such a component facilitates maintenance of the structural integrity of the biopharmaceutical drug, particularly during freezing and/or lyophilization and/or storage (especially when exposed to stress).

The liquid pharmaceutical composition may comprise one or more poylol stabilisers, though in preferred embodiments only a single polyol stabiliser is present.

Suitably, the polyol stabiliser is a polyol with 2 to 6 carbon atoms (C2-C6 polyol), more suitably 2 to 4 carbon atoms (C2-C4 polyol).

It was surprisingly found that, when combined with arginine and methionine, small polyols, such as propylene glycol and glycerol, have a better stabilizing effect at adalimumab formulations than large polyols, such as trehalose.

The polyol stabiliser is suitably selected from the group including fructose, mannose, rhamnose, galactose, glucose, sorbose, mannitol, sorbitol, arabinose, xylose, ribose, xylitol, ribitol, erythritol, threitol, glycerol, propylene glycol and ethylene glycol. More suitably, the polyol stabiliser is propylene glycol or glycerol. Most suitably, the polyol stabiliser is glycerol.

The polyol may be one or more polyols, wherein each polyol is suitably independently a polyol as defined herein. Insofar as the present application defines quantities (e.g. amounts, concentrations, or ratios) of a polyol, such quantities may be construed as quantities of the one or more polyols combined. In alternative embodiments, such quantities may be construed as quantities relating to just one or at least one of the one or more polyols. In certain embodiments the composition comprises one polyol in any one of the quantities defined herein.

Suitably, the liquid pharmaceutical composition comprises the polyol stabilizer(s) (most suitably glycerol) at a concentration of from about 50 to about 400 mM, more suitably from about 100 to about 200 mM, more suitably from about 110 to about 150 mM. In an embodiment, the polyol stabilizer(s) is present at a concentration of between 120 and 140 mM, most suitably about 130 mM. In an embodiment, glycerol is present at a concentration of 130 mM.

Suitably, the liquid pharmaceutical composition comprises the polyol stabilizer(s) (most suitably glycerol) at a concentration of from about 1 mg/mL to about 50 mg/mL, more suitably from about 5 mg/mL to about 20 mg/mL, more suitably from about 7.5 mg/mL to about 15 mg/mL. In an embodiment, the polyol stabilizer(s) is present at a concentration of between 9 mg/mL and 12.5 mg/mL, most suitably about 9.9 or 12 mg/mL. In a particular embodiment, glycerol is present at a concentration of 12 mg/mL.

Suitably, the liquid pharmaceutical composition comprises the polyol stabilizer(s) (most suitably glycerol) in a molar ratio of polyol stabilizer(s) to adalimumab of from about 10:1 to about 1000:1, more suitably from about 100:1 to about 300:1, more suitably from about 150:1 to about 250:1. In an embodiment, the polyol stabilizer(s) is present at a molar ratio of polyol stabilizer(s) to adalimumab of from about 175:1 to about 200:1, most suitably about 187:1. In an embodiment, glycerol is present at a molar ratio of glycerol to adalimumab of about 187:1.

In accordance with certain embodiments of the invention, the polyol (or the one or more polyols) may be (each independently) defined as set forth in any of, or any combination of, the following numbered paragraphs:

(1) a C2-C6 polyol—i.e. an aliphatic (linear or branched) or cyclic organic molecule comprising between 2 and 6 carbon atoms and at least two hydroxyl groups;
(2) a C2-C5 polyol, suitably a C2-C4 polyol, suitably a C2-C3 polyol;
(3) a polyol as defined herein comprising at most 5 hydroxyl groups, suitably at most 4 hydroxyl groups, suitably at most 3 hydroxyl groups, suitably two or three hydroxyl groups (no more and no fewer);
(4) a polyol free of any heteroatom except for oxygen;
(5) a polyol, wherein each and every oxygen atom within the polyol is a part of a hydroxyl group;
(6) a polyol free of any carbonyl and carboxy groups;
(7) a polyol free of any ionised or ionisable groups (especially at a pH between 3 and 8);
(8) a polyol having a molecular weight less than or equal to 167 g/mol, suitably less than or equal to 153 g/mol, suitably less than or equal to 137 g/mol, suitably less than or equal to 123 g/mol, suitably less than or equal to 107 g/mol, suitably less than or equal to 93 g/mol;
(9) a polyol having a molecular weight greater than or equal to 61 g/mol, suitably greater than or equal to 75 g/mol;
(10) a polyol that is a liquid at SATP (see definitions);
(11) a polyol that is a liquid at 0° C. at standard pressure (see definitions);
(12) a polyol that behaves as an antifreeze component within an aqueous solution;
(13) a polyol having a boiling point greater than or equal to 150° C. at standard pressure, suitably greater than or equal to 180° C., suitably greater than 250° C.;
(14) a polyol having a boiling point less than or equal to 300° C. at standard pressure, suitably less than or equal to 200° C.;
(15) a polyol having a melting point less than 25° C. at standard pressure, suitably less than or equal to 20° C.;
(16) a polyol having a melting point greater than or equal to −80° C. at standard pressure, suitably greater than or equal to 10° C.;
(17) a polyol free or substantially free of a polyol comprising 5 or more carbon atoms, suitably free or substantially free of a polyol comprising 4 or more carbon atoms;
(18) a polyol free or substantially free of a polyol comprising 5 or more hydroxyl groups, suitably free or substantially free of a polyol comprising 4 or more hydroxyl groups;
(19) a polyol free or substantially free of a polyol comprising 5 or more oxygen atoms, suitably free or substantially free of a polyol comprising 4 or more oxygen atoms;
(20) glycerol or an isomer thereof, or propylene glycol;
(21) glycerol;
(22) propylene glycol;
(23) a polyol as defined herein at a concentration of 50 to 200 mM, suitably 100 to 160 mM, suitably 120 to 140 mM;
(24) one or more polyols, each independently as defined herein, at a combined concentration of 50 to 200 mM, suitably 100 to 160 mM, suitably 120 to 140 mM;

Suitably, in the context of the invention, non-ionic surfactants (such as polysorbate(s) and poloxamer(s)) are not "polyols" as defined herein. As such, a "polyol" as defined herein may be considered a non-surfactant polyol.

Suitably, in the context of the invention, buffering species (such as tartrate) are not "polyols" as defined herein. As such, a "polyol" as defined herein may be considered a non-buffering polyol.

In a particular embodiment, the polyol or each polyol is a C2-C4 polyol with at most 4 hydroxyl groups.

In a particular embodiment, the polyol or each polyol is a C2-C4 polyol wherein each and every oxygen atom within the polyol is a part of a hydroxyl group.

In a particular embodiment, the polyol or each polyol has a molecular weight less than or equal to 107 g/mol and is a liquid at SATP.

Suitably, the weight ratio of adalimumab to polyol within the liquid pharmaceutical composition is between 100:1 and 1:1, suitably between 20:1 and 5:1, more suitably between 12:1 and 6:1, most suitably about 8:1 or about 10:1.

Suitably, the liquid pharmaceutical composition comprises the polyol and arginine (most suitably L-arginine) in a respective molar ratio of between about 50:1 and about 1:10, suitably between about 10:1 and about 1:1, suitably between about 3:1 and about 3:2, most suitably about 13:6. Suitably, the molar concentration of polyol is greater than the molar concentration of arginine.

Suitably, the liquid pharmaceutical composition comprises the polyol and methionine (most suitably L-methionine) in a respective molar ratio of between about 25:1 and about 1:5, suitably between about 10:1 and about 1:1, suitably between about 6:1 and about 3:1, most suitably about 13:3. Suitably, the molar concentration of polyol is greater than the molar concentration of methionine.

Suitably, the liquid pharmaceutical composition comprises the polyol and a combination of amino acids arginine (most suitably L-arginine) and methionine (most suitably L-methionine) in a respective molar ratio of polyol to the combination of amino acids between about 75:1 and about 1:5, suitably between about 20:1 and about 1:2, suitably between about 10:1 and about 1:1, suitably between about 2:1 and 1:2, most suitably about 13:9. Suitably, the molar concentration of polyol is greater than the molar concentration of the combination of the two amino acids.

As illustrated in the Example section, liquid pharmaceutical compositions of the invention including a polyol stabiliser as defined herein perform particularly well in stress tests, especially in relation to aggregation, fragmentation and protein unfolding, which can be important indicators of stability and drug product viability. Furthermore, liquid pharmaceutical compositions comprising C2-C6 polyols as the polyol stabiliser perform particularly well.

Diluent

The liquid pharmaceutical compositions of the invention may include any one or more pharmaceutically acceptable diluents, or mixture thereof. However, most suitably the liquid pharmaceutical composition is an aqueous pharmaceutical composition. Most suitably the diluent is water, and suitably water alone. The water is suitably water for injection (WFI).

Suitably the diluent may constitute the balance of ingredients in any liquid pharmaceutical composition, for instance so that the weight percentages total 100%. Suitably any concentrations given herein in relation to any component of the liquid pharmaceutical composition represent concentrations of said component in (and suitably dissolved in) the diluent in admixture with any other components.

Suitably, the liquid pharmaceutical composition comprises greater than or equal to 80 wt % water, suitably greater than or equal to 85 wt % water.

The liquid pharmaceutical composition of the invention is suitably a solution, and is suitably (substantially or entirely) free of particulates or precipitates.

Optional Additional Components

Buffer, Buffering Agent, and pH

Suitably, the liquid pharmaceutical composition is a buffered solution whose pH is stabilised by a buffering agent, suitably in combination with an acid/base conjugate of the buffering agent. As such, the liquid pharmaceutical composition suitably comprises a buffering agent as defined herein. Preferably, the liquid pharmaceutical composition additionally comprises an acid/base conjugate, wherein said acid/base conjugate corresponds to the conjugate acid or conjugate base of the buffering agent, depending on whether the buffering agent is itself a base or acid respectively. Collectively, the buffering agent and its acid/base conjugate may be considered a "buffer system". The liquid pharmaceutical composition thus suitably comprises a "buffer system" (suitably comprising a buffering agent(s) and an acid/base conjugate(s) thereof), and any concentrations stipulated in relation to the buffer system generally relate to the combined concentrations of the buffering agent(s) and any acid/base conjugate(s) thereof. Any "buffer system" suitably comprises a weak acid and a weak base (see above definitions).

Suitably, the buffering agent is an acetate buffering agent. Suitably the acetate buffering agent is an acetate salt, suitably comprising anionic acetate (i.e. AcO—) and one or more pharmaceutically acceptable countercations. A suitable acetate salt may include a metal acetate salt (e.g. an alkali metal acetate or an alkaline earth metal acetate), or a non-metal acetate salt (e.g. ammonium acetate, triethylammonium acetate). In a particular embodiment, the buffering agent (and the acetate salt) is sodium acetate.

Suitably, the liquid pharmaceutical composition comprises an acid/base conjugate of the buffering agent, most suitably acetic acid as the conjugate acid of an acetate salt. The combination of the buffering agent and its acid/base conjugate constitute a buffer system. Suitably, the liquid pharmaceutical composition comprises the buffering agent and its corresponding acid/base conjugate, suitably such that together the buffering agent and its acid/base conjugate are present at a level (i.e. absolute amount or concentration) and in a relative amount (or concentration) sufficient to provide the desired pH for the composition. The buffer system may be formed by simply mixing the buffering agent with its acid/base conjugate or may alternatively be formed by mixing an acid or base with either the buffering agent or its acid/base conjugate in order to form in situ the desired mixture of buffering agent and acid/base conjugate. For example, the buffer system may be formed by simply mixing the acetate buffering agent (e.g. sodium acetate) with its acid/base conjugate (i.e. acetic acid), suitably in a ratio appropriate to furnish the desired pH. Alternatively, the buffer system may be formed by adding a base (e.g. sodium hydroxide) to the acid/base conjugate (i.e. acetic acid) of the acetate buffering agent, suitably in an amount appropriate to furnish the desired pH and mixture of the buffering agent (e.g. sodium acetate) and corresponding acid/base conjugate (i.e. acetic acid). Alternatively, either method of forming the buffer system may be employed, and pH may be judiciously adjusted by either adding further acid (suitably strong acid, such as HCl) or further base (suitably strong base, such as sodium hydroxide).

Most suitably, the buffer system is an acetate buffer system, suitably comprising an acetate salt and acetic acid.

Suitably, the liquid pharmaceutical composition comprises at most one buffering agent. Suitably, the liquid pharmaceutical composition comprises at most one buffer system.

Suitably, where a buffer system is present, the said buffer system is formed in a manner that yields substantially no skin-irritants, such as sodium chloride, as by-products. Most suitably, the buffer system is formed in a manner than yields less than 2.7 mM sodium chloride, suitably less than 2 mM sodium chloride, suitably less than 1 mM sodium chloride, suitably less than 0.1 mM sodium chloride, most suitably (substantially) no sodium chloride. For instance, though an acetate buffer may be formed by acidification of an acetate salt (e.g. sodium acetate, or a hydrate thereof) with hydrochloric acid, this will inevitably yield some chloride salt by-products (e.g. sodium chloride). Since the present invention facilitates viable formulations with minimal quantities of skin-irritants, such as chloride salts, it is desirable to eliminate or limit their emergence during buffer formation. As such, the buffer system is most suitably formed through judicious basification (e.g. with sodium hydroxide) of the conjugate acid of the buffer system (e.g. acetic acid) or through judicious mixing of appropriate quantities of conjugate acid and conjugate base (e.g. acetic acid/sodium acetate). In a particular embodiment, an acetate buffer system is formed by treating a given quantity of acetic acid (suitably mixed with other ingredients and/or excipients) with an appropriate amount of a basifying agent (suitably sodium hydroxide or other oxide or hydroxide salt) to achieve the desired pH.

Suitably, the liquid pharmaceutical composition has a pH greater than or equal to 4.0. Suitably, the liquid pharmaceutical composition has a pH less than or equal to 6.0.

In a particular embodiment, especially where the buffering agent is an acetate buffering agent, the liquid pharmaceutical composition has a pH between 4.5 and 5.5. In a particular embodiment, the liquid pharmaceutical composition has a pH between 4.9 and 5.1. In a particular embodiment, the liquid pharmaceutical composition has a pH of about 5.0.

In a particular embodiment, especially where the buffering agent is an acetate buffering agent and/or especially where the composition comprises at most 30 mM (though more suitably at most 20 mM or 10 mM) tonicifier (especially where the tonicifier in question is sodium chloride or another skin-irritating tonicifier), the liquid pharmaceutical composition has a pH between 4.8 and 5.8. In a particular embodiment, the liquid pharmaceutical composition has a pH between 4.9 and 5.3, suitably between 5.0 and 5.4, suitably between 5.1 and 5.3. In a particular embodiment, the liquid pharmaceutical composition has a pH of about 5.2. The pH may suitably be pH 5.0+/−0.5.

Without wishing to be bound by theory, it is thought that implementing the present invention allows formulations to be judiciously modified in a manner that reduces skin pain/irritation experienced during subcutaneous injection without compromising overall stability and efficacy. For example, the incorporation of arginine and methionine either in combination with each other and/or in combination with a polyol, can open up the possibility of reducing buffer concentrations, even in more concentrated adalimumab formulations.

Suitably, the liquid pharmaceutical composition comprises a buffer system (suitably an acetate buffer system comprising an acetate buffering agent) at a concentration of from about 1 to about 50 mM. In an embodiment, the buffer system is present at a concentration of between 5 and 10 mM, most suitably about 8 mM. In an embodiment, the buffer system is present at a concentration of 8 mM. Most preferably, the liquid pharmaceutical composition comprises a sodium acetate/acetic acid buffer system at a concentration of 8 mM. This includes where the "buffering agent(s)" (e.g. sodium acetate) is formed by the addition of a strong base (e.g. sodium hydroxide) to the conjugate acid of the buffering agent(s) (e.g. acetic acid). This latter embodiment is expected to cause reduced skin irritation upon injection as well as pain around the injection site as compared to the aforementioned commercial adalimumab formulation, since the latter embodiment has a reduced buffer concentration and avoids the citrate and phosphate buffer components that are known to cause pain upon subcutaneous injection (Kappelgaard et al. (2004) Horm. Res. 62 Suppl 3:98-103 and Fransson et al. (1996) J. Pharm. Pharmacol. 48:1012-1015).

Suitably, the liquid pharmaceutical composition comprises the buffering species (suitably acetate buffering species) at a concentration of from about 0.05 mg/mL to about 3.0 mg/mL. In an embodiment, the buffering species are present at a concentration of between 0.1 mg/mL and 1.50 mg/mL, suitably between 0.4 mg/mL and 0.6 mg/mL, most suitably about 0.5 mg/mL. This includes where the "buffering agent" (e.g. sodium acetate) is formed by the addition of a strong base (e.g. sodium hydroxide) to the conjugate acid of the buffering agent (e.g. acetic acid).

Suitably, the liquid pharmaceutical composition comprises the buffer system (suitably the acetate buffer system) in a molar ratio of buffer system to adalimumab of from about 1:1 to about 100:1. In an embodiment, the buffer system is present in a molar ratio of buffer system to adalimumab of from about 5:1 to about 30:1, most suitably about 11:1. In an embodiment, the buffer system is present at a concentration of 11:1. This includes where the "buffering agent(s)" (e.g. sodium acetate) is formed by the addition of a strong base (e.g. sodium hydroxide) to the conjugate acid of the buffering agent (e.g. acetic acid).

As illustrated in the Example section, liquid pharmaceutical compositions of the invention including an acetate buffer system perform particularly well in stress tests, especially in relation to fragmentation and protein unfolding, which can be important indicators of stability and drug product viability. Furthermore, liquid pharmaceutical compositions whose acetate buffer system maintains a steady pH 5.2 perform particularly well.

Tonicifier

The liquid pharmaceutical composition of the invention may suitably comprise a "tonicity modifier" (or "tonicifier") or one or more tonicifiers, suitably as defined herein.

The inclusion of a tonicifier suitably contributes to (or increases) the overall osmolality and osmolarity of the composition. Suitably a tonicifier is present within the composition in a quantity or concentration sufficient for the composition to be (substantially) isotonic with body fluids. Suitably a tonicifier is present within the composition in a quantity or concentration sufficient for the composition to have an osmolarity or osmolality within a range defined herein.

Any suitable tonicifier may be used. However, suitably the tonicifier is selected from the group including water-soluble metal salts (e.g. sodium chloride, potassium chloride, magnesium chloride, calcium chloride), water-soluble tonicifying sugars/sugar alcohols (e.g. glucose, sucrose, mannitol), and/or other water-soluble polyols. Suitably the tonicifier(s) is non-buffering (i.e. gives rise to little or no buffering effect). As such, any metal salt tonicifiers are suitably not buffering agents.

The liquid pharmaceutical composition may comprise one or more tonicifiers, though preferably only a single "tonicifier" as such is present (notwithstanding any tonicifying effects imparted to the composition by components intended to serve another function as defined herein).

Most preferably, the tonicifier is or comprises a metal salt (preferably a non-buffering water-soluble metal salt). Suitably, said metal salt is or comprises a metal halide, suitably an alkali or an alkaline earth metal halide, suitably an alkali metal chloride.

In a particular embodiment, the tonicifier is or comprises sodium chloride. In a particular embodiment, the tonicifier is sodium chloride. Sodium chloride is a particularly advantageous stabiliser for use alongside an acetate buffering agent/buffer system in liquid adalimumab formulations.

Without wishing to be bound by theory, it is thought that implementing the present invention allows formulations to be judiciously modified in a manner that reduces skin pain/irritation experienced during subcutaneous injection without compromising overall stability and efficacy. For example, the incorporation of arginine and methionine either in combination with each other and/or in combination with a polyol, can open up the possibility of reducing tonicifier concentrations, even in more concentrated adalimumab formulations.

Suitably, the liquid pharmaceutical composition comprises the tonicifier(s) (most suitably sodium chloride) at a concentration of from about 5 to about 100 mM, more suitably from about 10 to about 50 mM, most suitably about 30 mM. In an embodiment, sodium chloride is present at a concentration of 30 mM.

Suitably, the liquid pharmaceutical composition comprises the tonicifier(s) (most suitably sodium chloride) at a concentration of from about 0.5 mg/mL to about 10 mg/mL, more suitably from about 1 mg/mL to about 5 mg/mL, more suitably from about 1.5 mg/mL to about 2 mg/mL. In an embodiment, the tonicifier(s) is present at a concentration of about 1.75 mg/mL. Most suitably, sodium chloride is present at a concentration of 1.75 mg/mL. The latter embodiment has a sodium chloride concentration which is much lower than the sodium chloride concentration of the aforementioned commercial adalimumab formulation. The lower sodium chloride concentration is expected to reduce the injection site pain.

Suitably, the liquid pharmaceutical composition comprises the tonicifier(s) (most suitably sodium chloride) in a molar ratio of tonicifier to adalimumab of from about 10:1 to about 200:1, more suitably from about 20:1 to about 100:1, more suitably from about 30:1 to about 50:1. In an embodiment, sodium chloride is present at a molar ratio of sodium chloride to adalimumab of about 43:1.

Suitably, the weight ratio of adalimumab to tonicifier (most suitably sodium chloride) within the liquid pharmaceutical composition is between 500:1 and 10:1, suitably between 200:1 and 20:1, more suitably between 100:1 and 50:1, most suitably about 57:1.

Suitably the tonicifier(s) (most suitably sodium chloride) is present at a concentration not exceeding 100 mM, suitably not exceeding 70 mM, more suitably not exceeding 50 mM, more suitably not exceeding 40 mM. Suitably the liquid pharmaceutical composition may be free or substantially free of a tonicifier, especially a skin-irritating tonicifier, for example, sodium chloride and/or other metal salt tonicifiers. In a particular embodiment, the liquid pharmaceutical composition is free or substantially free of sodium chloride. In a particular embodiment, the liquid pharmaceutical composition is free of, substantially free of, or comprises at most 40 mM of a tonicifier (e.g. sodium chloride). In a particular embodiment, the liquid pharmaceutical composition is free of, substantially free of, or comprises at most 32 mM of a tonicifier (e.g. sodium chloride). In a particular embodiment, the liquid pharmaceutical composition is free of, substantially free of, or comprises at most 20 mM of a tonicifier (e.g. sodium chloride).

As illustrated in the Example section, liquid pharmaceutical compositions of the invention including a tonicifier as defined herein perform particularly well in stress tests, especially in relation to aggregation, fragmentation and protein unfolding, which can be important indicators of stability and drug product viability. Furthermore, liquid pharmaceutical compositions comprising sodium chloride, particularly in an amount range as stipulated, perform particularly well.

Surfactant

The liquid pharmaceutical composition of the invention suitably comprises a surfactant or one or more surfactants, suitably as defined herein.

The inclusion of a surfactant suitably contributes to stabilisation of the adalimumab protein.

Any suitable surfactant may be used. However, suitably the surfactant is a non-ionic surfactant, most suitably a polysorbate (polyoxyethylene glycol sorbitan alkyl esters) or poloxamer surfactant.

Though one or more surfactants may be included within the liquid pharmaceutical composition of the invention, most suitably only a single surfactant is present, most suitably a single non-ionic surfactant (suitably as defined herein).

The surfactant(s) are suitably selected from polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate), poloxamer 188 and poloxamer 407.

In a particular embodiment, the surfactant is polysorbate 80, polysorbate 20 or poloxamer 188. In a particular embodiment, the surfactant is polysorbate 20. In a particular embodiment, the surfactant is poloxamer 188.

Suitably, the liquid pharmaceutical composition comprises the surfactant(s) (most suitably polysorbate 20) at a concentration of from about 0.1 to about 100 mM, more suitably from about 0.5 to about 20 mM, more suitably from about 0.7 to about 1.0 mM. In an embodiment, the surfactant(s) is present at a concentration of about 0.8 mM. In an embodiment, polysorbate 20 is present at a concentration of 0.8 mM.

Suitably, the liquid pharmaceutical composition comprises the surfactant(s) (most suitably polysorbate 20) at a concentration of from about 0.1 mg/mL to about 10 mg/mL, more suitably from about 0.5 mg/mL to about 2 mg/mL, more suitably between about 0.9 mg/mL and about 1.1 mg/mL, most suitably about 1.0 mg/mL. In a particular embodiment, polysorbate 20 is present at a concentration of 1.0 mg/mL.

Suitably, the liquid pharmaceutical composition comprises the surfactant(s) (most suitably polysorbate 20) in a molar ratio of surfactant(s) to adalimumab of from about 1:2 to about 50:1, more suitably from about 1:1 to about 30:1. In an embodiment, the surfactant(s) is present at a molar ratio of surfactant(s) to adalimumab of from about 1:1 to about 1.3:1, most suitably about 1.15:1. In an embodiment, polysorbate 20 is present at a molar ratio of polysorbate 20 to adalimumab of about 1.17:1.

As illustrated in the Example section, liquid pharmaceutical compositions of the invention including a surfactant as defined herein perform particularly well in stress tests, especially in relation to aggregation, fragmentation and protein unfolding, which can be important indicators of stability and drug product viability. Furthermore, liquid pharmaceutical compositions comprising polysorbate 20, particularly in an amount range as stipulated, perform particularly well.

Specific embodiments

In a particular embodiment, the liquid pharmaceutical composition of the invention comprises:
(a) adalimumab;
(b) a combination of arginine and methionine in a molar ratio between 1:1 and 3:1, wherein arginine and methionine are present at a combined concentration between 50 mM and 130 mM (suitably 80-100 mM);
wherein the composition has a pH between 4.0 and 6.0.

In a particular embodiment, the liquid pharmaceutical composition of the invention comprises:
(a) 25-125 mg/mL adalimumab;
(b) a combination of arginine and methionine in a molar ratio between 1:1 and 3:1, wherein arginine and methionine are present at a combined concentration between 50 mM and 130 mM (suitably 80-100 mM);
wherein the composition has a pH between 4.8 and 5.2.

In a particular embodiment, the liquid pharmaceutical composition of the invention comprises:
(a) adalimumab;
(b) a combination of arginine and methionine;
(c) a polyol selected from glycerol and propylene glycol;
wherein the composition has a pH between 4.0 and 6.0.

In a particular embodiment, the liquid pharmaceutical composition of the invention comprises:
(a) adalimumab;
(b) arginine, methionine, or a combination thereof, at a (combined) concentration between 10 mM and 250 mM, and the weight ratio of adalimumab to the combination of amino acids between 30:1 and 3:1;
(c) a C2-C5 polyol with at most 4 hydroxyl groups, wherein the weight ratio of adalimumab to polyol is between 20:1 and 5:1;
wherein the composition has a pH between 4.5 and 5.5.

In a particular embodiment, the liquid pharmaceutical composition of the invention comprises:
(a) adalimumab;
(b) a combination of arginine and methionine in a molar ratio between 1:5 and about 5:1, a combined concentration between 10 mM and 250 mM, and the weight ratio of adalimumab to the combination of amino acids between 30:1 and 3:1;
(c) a C2-C5 polyol with at most 4 hydroxyl groups, wherein the molar ratio of polyol to the combination of amino acids is between 10:1 and 1:1;
wherein the composition has a pH between 4.0 and 6.0.

In a particular embodiment, the liquid pharmaceutical composition of the invention comprises:
(a) 25 to 125 mg/mL adalimumab;
(b) a combination of arginine and methionine in a molar ratio between 1:1 and 3:1, wherein arginine and methionine are present at a combined concentration between 50 mM and 130 mM (suitably 80-100 mM);
(c) a C2-C3 polyol with at most 3 hydroxyl groups, wherein the molar ratio of polyol to the combination of amino acids is between 10:1 and 1:1;
wherein the composition has a pH between 4.5 and 5.5.

In a particular embodiment, the liquid pharmaceutical composition comprises:
(a) 100 pbw adalimumab;
(b) 1-20 pbw arginine;
(c) 1-10 pbw methionine; and
(d) 1-20 pbw polyol selected from glycerol or propylene glycol.

In a particular embodiment, the liquid pharmaceutical composition comprises:
(a) 100 pbw adalimumab;
(b) 5-15 pbw arginine;
(c) 2-8 pbw methionine; and
(d) 5-15 pbw polyol selected from glycerol or propylene glycol.

In a particular embodiment, the liquid pharmaceutical composition comprises:
(a) 100 pbw adalimumab;
(b) 8-12 pbw arginine;
(c) 4-5 pbw methionine; and
(d) 8-13 pbw polyol selected from glycerol or propylene glycol.

The above embodiments may suitably further comprise a tonicifier (which is most suitably sodium chloride) but suitably the concentration of the tonicifier is at most 50 mM, suitably at most 40 mM. Moreover, such embodiments suitably comprise a buffer system (which is suitably an acetate buffer system), though suitably the concentration of the buffer system is at most 10 mM. Where sodium chloride is present in a liquid pharmaceutical composition, it is suitably present in a concentration between 20 and 40 mM, most suitably about 30 mM.

The above specific embodiments may suitably be free of, substantially free of, or comprise at most 40 mM (more suitably at most 30 mM, more suitably at most 20 mM, more suitably at most 10 mM) of a tonicifier (which tonicifier is most suitably sodium chloride). Suitably where the composition comprises at or below 20 mM sodium chloride, and especially where the composition is free of or substantially free of sodium chloride, the pH of said composition is between pH 4.8 and 5.4, suitably between 4.9 and 5.3, suitably between 5.1 and 5.3, most suitably pH 5.2 (suitably +/−0.3). As such, any pH specified above may be adjusted to be within one of these ranges. Moreover, such embodiments suitably comprise a buffer system (which is suitably an acetate buffer system), though suitably the concentration of the buffer system is at most 10 mM.

The present invention suitably allows adalimumab compositions to be formulated with reduced amounts of injection-pain-inducing compounds, such as tonicifiers and buffers.

Method of Stabilising Antibody

The present invention also provides a method of stabilising liquid adalimumab compositions (chemically and/or physically), comprising mixing adalimumab with any relevant components required to form a liquid pharmaceutical composition as defined herein. Different embodiments will suitably require different combinations of components to be mixed, potentially in different amounts, and the skilled person can readily deduce such combinations and amounts by reference to the foregoing disclosure relating to the liquid pharmaceutical composition. Such different combinations of components may stabilise liquid adalimumab compositions in different respects. For instance, mixing adalimumab with the aforementioned components to form a liquid pharmaceutical composition as defined herein may stabilise adalimumab by:
  i) Increasing the protein unfolding temperature of adalimumab;
  ii) Inhibiting the formation of aggregates;
  iii) Inhibiting the formation of fragments;
  iv) Inhibiting the formation of deamidated species or isomers;
  v) Inhibiting the formation of sub-visible particles (either ≤25 microns or ≤10 microns);
  vi) Inhibiting turbidification;
  vii) Inhibiting pH changes;
  viii) Inhibiting photo-oxidation; and/or
  ix) Reducing instability upon freeze/thaw cycles.

As such, the present invention provides a method of achieving one, some, or all of the following benefits:
  i) Increased protein unfolding temperatures for adalimumab;
  ii) Inhibition of formation of aggregates;
  iii) Inhibition of formation of fragments;
  iv) Inhibiting the formation of deamidated species or isomers;
  v) Inhibition of formation of sub-visible particles (either ≤25 microns or ≤10 microns);
  vi) Inhibition of turbidification;
  vii) Inhibition of pH changes;
  viii) Inhibition of photo-oxidation;
  ix) Reduced instability upon freeze/thaw cycles; and/or
  x) Stabilisation of the isoform profile (especially with respect to the "main peak" as defined herein);
the method comprising manufacturing a liquid pharmaceutical composition of adalimumab as defined herein.

Suitably, the liquid pharmaceutical compositions of the invention have a shelf life of at least 6 months, suitably at least 12 months, suitably at least 18 months, more suitably at least 24 months. Suitably, the liquid pharmaceutical compositions of the invention have a shelf life of at least 6 months, suitably at least 12 months, suitably at least 18 months, more suitably at least 24 months, at a temperature of 2-8° C.

Enabling the Skilled Person to Optimise Key Stability Properties

The novel combination of components disclosed for use in liquid pharmaceutical compositions of the invention enables the skilled person to produce (and judiciously fine-tune) compositions which exhibit comparable or enhanced properties relative to compositions of the prior art. In particular, the present disclosure now provides the skilled person with all the necessary tools to optimise formulation stability, and in particular optimise one or more of: inhibition of aggregation, fragmentation, deamidation, isomerisation, protein unfolding, precipitation, pH slippage, and oxidation (especially photo-oxidation). Furthermore, the skilled person is given guidance on how to achieve such optimisations (through judiciously varying the compositions) and how, in the process, to minimise any detrimental side-effects. The present disclosure enables the skilled person to work across the scope of the invention to produce a variety of specific compositions which exhibit comparable or improved properties relative to compositions of the prior art, and this can be achieved using fewer components.

Method of Manufacturing a Liquid Pharmaceutical Composition

The present invention provides a method of manufacturing a liquid pharmaceutical composition, suitably as defined herein. The method suitably comprises mixing together, in any particular order deemed appropriate, any relevant components required to form a liquid pharmaceutical composition as defined herein. The skilled person may refer to the Examples or techniques well known in the art for forming liquid pharmaceutical compositions (especially those for injection via syringe). Different embodiments will suitably require different combinations of components to be mixed, potentially in different amounts. The skilled person can readily deduce such combinations and amounts by reference to the foregoing disclosure relating to the liquid pharmaceutical composition.

Suitably the method involves mixing together the relevant components suitably, in a diluent (e.g. water), suitably so that all of the components are (substantially or entirely) dissolved in the diluent.

The method may involve first preparing a pre-mixture (or pre-solution) of some or all components (optionally with some or all of the diluent) excluding adalimumab, and adalimumab may then itself (optionally with or pre-dissolved in some of the diluent) be mixed with the pre-mixture (or pre-solution) to afford the liquid pharmaceutical composition, or a composition to which final components are then added to furnish the final liquid pharmaceutical composition. Most suitably, the pre-mixture contains all components except for the adalimumab and optionally also some diluent (which may be used to pre-dissolve adalimumab), suitably so that adalimumab is added to a mixture which offers optimal stabilisation of adalimumab. Suitably the aforementioned pre-mixture is prepared with the desired pH for the final liquid pharmaceutical formulation.

Suitably, the method involves forming a buffer system, suitably a buffer system comprising a buffering agent as defined herein. The buffer system is suitably formed in a pre-mixture prior to the addition of adalimumab, though the buffer system may optionally be formed with adalimumab present. The buffer system may be formed through simply mixing the buffering agent (supplied ready-made) with its acid/base conjugate (suitably in appropriate relative quantities to provide the desired pH—this can be determined by the skilled person either theoretically or experimentally). In the case of an acetate buffer system, this means mixing sodium acetate with acetic acid. Alternatively, the buffer system may be formed through adding a strong acid (e.g. HCl) to the buffering agent (e.g. sodium acetate) in order to form in situ the acid/base conjugate (e.g. acetic acid) (again suitably in appropriate relative quantities to provide the desired pH). Alternatively, the buffer system may be formed through adding a strong base (e.g. sodium hydroxide) to the acid/base conjugate (e.g. acetic acid) of the buffering agent (e.g. sodium acetate) in order to form in situ the buffering agent (again suitably in appropriate relative quantities to provide the desired pH). The pH of either the pre-mixture of final liquid pharmaceutical composition may be judiciously adjusted by adding the required quantity of strong base or strong acid, or even a quantity of buffering agent or acid/base conjugate.

In certain embodiments, the buffering agent and/or buffer system is pre-formed as a separate mixture, and the buffer system is transferred to a precursor of the liquid pharmaceutical composition (comprising some or all components save for the buffering agent and/or buffer system, suitably comprising adalimumab and potentially only adalimumab) via buffer exchange (e.g. using diafiltration until the relevant concentrations or osmolality is reached). Additional excipients may be added thereafter if necessary in order to produce the final liquid pharmaceutical composition. The pH may be adjusted once or before all the components are present.

Any, some, or all components may be pre-dissolved or pre-mixed with a diluent prior to mixing with other components.

The final liquid pharmaceutical composition may be filtered, suitably to remove particulate matter. Suitably filtration is through filters sized at or below 1 μm, suitably at 0.22 μm. Suitably, filtration is through either PES filters or PVDF filters, suitably with 0.22 μm PES filters.

The present invention also provides a liquid pharmaceutical composition obtainable by, obtained by, or directly obtained by the method of manufacture herein described.

Drug-delivery Device

The present invention provides a drug delivery device comprising a liquid pharmaceutical composition as defined herein. Suitably the drug delivery device comprises a chamber within which the pharmaceutical composition resides. Suitably the drug delivery device is sterile.

The drug delivery device may be a vial, ampoule, syringe, injection pen (e.g. essentially incorporating a syringe), or intravenous bag. Most suitably the drug delivery device is a syringe, suitably an injection pen. Suitably the syringe is a glass syringe. Suitably the syringe comprises a needle, suitably a 29G½" needle.

The present invention provides a method of manufacturing a drug delivery device, suitably as defined herein, the method comprising incorporating a liquid pharmaceutical composition as defined herein within a drug delivery device. Such manufacture typically involves charging the liquid pharmaceutical composition as defined herein to a syringe, suitably via a needle affixed thereto. The needle may thereafter be removed, replaced, or remain.

According to another aspect of the present invention there is provided a drug delivery device obtainable by, obtained by, or directly obtained by a method of manufacture defined herein.

Package

The present invention provides a package comprising a liquid pharmaceutical composition as defined herein. Suitably the package comprises a drug delivery device as defined herein, suitably a plurality of drug delivery devices. The package may comprise any suitable container for containing one or more drug delivery devices.

The present invention provides a method of manufacturing a package, the method comprising incorporating a liquid pharmaceutical composition as defined herein within a package. Suitably this is achieved by incorporating said liquid pharmaceutical composition within one or more drug delivery devices, and thereafter incorporating the one or more pre-filled drug delivery devices into a container present within the package.

The present invention provides a package obtainable by, obtained by, or directly obtained by a method of manufacture defined herein.

Kit of Parts

The present invention provides a kit of parts comprising a drug delivery device (without the liquid pharmaceutical composition incorporated therein), a liquid pharmaceutical composition as defined herein (optionally contained in a separate package or container), and optionally a set of instructions with directions regarding the administration (e.g. sub-cutaneous) of the liquid pharmaceutical composition. The user may then fill the drug delivery device with the liquid pharmaceutical composition (which may be provided in a vial or ampoule or such like) prior to administration.

Uses of Pharmaceutical Liquid Composition and Methods of Treatment

According to another aspect of the present invention there is provided a method of treating a disease or medical disorder; a liquid pharmaceutical composition for use in therapy; a use of a liquid pharmaceutical composition in the manufacture of a medicament for the treatment of a disease or disorder; a method of treating a tumour necrosis factor-alpha (TNF-α)-related autoimmune disease; a liquid pharmaceutical composition for use in the treatment of a tumour necrosis factor-alpha (TNF-α)-related autoimmune disease; a use of a liquid pharmaceutical composition in the manufacture of a medicament for the treatment of a tumour necrosis factor-alpha (TNF-α)-related autoimmune disease; a method of treating rheumatoid arthritis, psoriatic arthritis, ankylosing spondylitis, Crohn's disease, ulcerative colitis, psoriasis, hidradenitis suppurativa, uveitis and/or juvenile idiopathic arthritis; a liquid pharmaceutical composition for use in the treatment of rheumatoid arthritis, psoriatic arthritis, ankylosing spondylitis, Crohn's disease, ulcerative colitis, psoriasis, hidradenitis suppurativa, uveitis and/or juvenile idiopathic arthritis; and a use of a liquid pharmaceutical composition in the manufacture of a medicament for the treatment of rheumatoid arthritis, psoriatic arthritis, ankylosing spondylitis, Crohn's disease, ulcerative colitis, psoriasis, hidradenitis suppurativa, uveitis and/or juvenile idiopathic arthritis; as defined herein.

The liquid pharmaceutical compositions defined herein may be used to treat any one or more of the aforementioned diseases or medical disorders. In a particular embodiment, the liquid pharmaceutical compositions are used to treat rheumatoid arthritis, Crohn's disease and psoriasis.

The liquid pharmaceutical compositions are suitably parenterally administered, suitably via sub-cutaneous injection.

EXAMPLES

Materials

The following materials were used in the preparation of formulations described in the Examples that follow:

| Chemical | Supplier |
| --- | --- |
| Sodium acetate, trihydrate | Sigma |
| L-Arginine | Sigma |
| L-Methionine | Sigma |
| Sodium chloride | Sigma |
| Trehalose | Sigma |
| Propylene glycol | Sigma |
| Glycerol | Sigma |
| Polysorbate 20 | Sigma |
| Water for injection | HyClone |

Analytical Techniques and Protocols

The following analytical methods of protocols were employed, in the Examples and Screening Experiments which follow, for the reasons stated in the table below:

| Analytical Method | Scope of the test |
| --- | --- |
| SEC | Quantification of soluble aggregates |
| IEX-HPLC | Quantification of acidic and basic species |
| Visual inspection | Appearance, assessment of particle formation |

The individual protocols for each of the above analytical methods are described in turn below, and references in the Examples and Screening Experiments to any such analytical methods used these protocols.

Visual Inspection

Visible particles are suitably detected using the 2.9.20. European Pharmacepoeia Monograph (Particulate Contamination: Visible Particles). The apparatus required consists of a viewing station comprising:
- a matt black panel of appropriate size held in a vertical position
- a non-glare white panel of appropriate size held in a vertical position next to the black panel
- an adjustable lampholder fitted with a suitable, shaded, white-light source and with a suitable light diffuser (a viewing illuminator containing two 13 W fluorescent tubes, each 525 mm in length, is suitable). The intensity of illumination at the viewing point is maintained between 2000 lux and 3750 lux.

Any adherent labels are removed from the container and the outside washed and dried. The container is gently swirled or inverted, ensuring that air bubbles are not introduced, and observed for about 5 s in front of the white panel. The procedure is repeated in front of the black panel. The presence of any particles is recorded. Samples that were either visually clear and samples that contained a very small number of minor particles were classed as "Pass". Samples that contained either larger particles or a larger number of particles, including opalescent samples, were classed as "Fail".

Size Exclusion Chromatography (SEC)

High performance size exclusion chromatography of adalimumab preparations is performed using the Dionex Ultimate 3000 UHPLC® focused system with a 4 μm phase diol Silica 250 Å pore packing material in a 300 mm by 4.6 mm column. The column is equilibrated in 50 mM sodium phosphate buffer, 400 mM sodium perchlorate, pH 6.3 mobile phase. Flow rate is 0.35 mL/min and UV detection (214 nm) is used. Injection volume is 20 μL. All analyses are performed at ambient temperature.

Ion-Exchange Chromatography (IEX-HPLC)

High performance ion exchange chromatography of adalimumab preparations is performed using the Agilent technologies 1200 series HPLC® system with a 7 μm particle in a 100 mm by 4.6 mm column. The column is equilibrated in 20 mM Tris pH 8.3 mobile phase and elution is performed with a gradient method by 20 mM Tris pH 8.3, 0.5 M NaCl. Flow rate is 1 mL/min and UV detection (230 nm) is used. Injection volume is 50 μL. All analyses are performed at 25° C.

Sample Preparation

Two different methods were used to prepare 100 mg/ml samples of adalimumab from a 60 mg/ml stock solution:

Tangental Flow Filtration (TFF)

TFF equipment: KR2i TFF System® (SpectrumLabs) was used in connection with D02-E030-05-N (30 kDa pore) TFF column (SpectrumLabs). The stock solution of adalimumab was diafiltered against 10 mM sodium acetate (pH 5.0), whilst increasing adalimumab concentration to 150 mg/ml. Following the final sample concentration a solution containing concentrated excipients was added to achieve 100 mg/ml adalimumab and the correct final concentration of each excipient.

Ultracentrifugation

The stock solution of adalimumab (60 mg/ml, 15 ml) was placed in an Amicon tube (30 kDa molecular weight cut-off). The tube was ultracentrifuged for 30 minutes at 21° C., 2000 g. At this point, the volume was reduced to 5 ml (i.e. 3-fold concentration of adalimumab). 10 mM of acetate buffer (10 mM) was added and the process was repeated 4 times. Following the final sample concentration a solution containing concentrated excipients was added to achieve 100 mg/ml adalimumab and the correct final concentration of each excipient.

Acetate Buffers

The acetate buffers used in the above sample preparations were produced by one of two methods. One method starts with sodium acetate and acidifies down to a desired pH, whilst the other starts with acetic acid and basifies up to a desired pH.

When an example formulation (e.g. Examples 1-3 below) stipulates sodium acetate alongside a pH, the corresponding acetate buffer was prepared through acidifying the stipulated concentration of sodium acetate with a judicious amount of hydrochloric acid to yield the desired pH.

When an example formulation (e.g. Example 4 below) stipulates acetic acid alongside a pH, the corresponding acetate buffer was prepared through basifying the stipulated concentration of acetic acid with a judicious amount of sodium hydroxide to yield the desired pH.

Example 1

Investigation of the Effect of Arginine and Methionine on Stability of Adalimumab The effect of arginine and methionine on stability of adalimumab (100 mg/ml) during storage at 40° C. was assessed. Samples were prepared by the TFF process. Aggregation of adalimumab was assessed by SEC, visual assessment and IEX-HPLC prior to and following storage at 40° C. for 4 weeks. The effect was tested in a background formulation comprising:
- sodium acetate (8 mM)
- sodium chloride (34 mM)
- trehalose (134 mM)
- polysorbate 20 (1 mg/ml)
- water for injection
- pH 5.0

Results are shown in Table 1. The rate of increase in HMWS was reduced in the presence of arginine (66 mM). Addition of methionine to the arginine-containing formulation caused further reduction in the rate of HMWS increase. The effect appeared to be concentration-dependent, higher concentration of methionine leading to greater reduction in HMWS. Similar effects of arginine and methionine were observed on the chemical stability of adalimumab. The retention of the main peak on the IEX-HPLC chromatogram was greater in the presence of arginine compared with arginine-free formulation. Addition of methionine to the arginine-containing formulation resulted in further stability improvement. All formulations tested passed the Visual inspection test with a very small number of minor particles being observed following storage at 40° C. for 4 weeks.

TABLE 1

Effect of methionine and arginine on physical and chemical stability of adalimumab (100 mg/ml) following storage at 40° C. for 4 weeks. Physical stability was assessed by the increase in % HMWS and by visual assessment. Chemical stability is expressed as decrease in the main peak on the IEX-HPLC chromatogram. All formulations contained sodium acetate (8 mM), trehalose (134 mM), sodium chloride (34 mM), polysorbate 20 (1 mg/ml) and water for injection and were adjusted to pH 5.0. Pass = virtually clear solution free of visible particles; Pass (—) = very small number of minor particles; Fail = formation of particles and/or opalescence.

| Additive | Increase in HMWS (%) | Visual assessment | Decrease in IEX-HPLC main peak (%) |
|---|---|---|---|
| No additive | 0.938 | Pass (—) | 28.63 |
| Arginine (66 mM) | 0.687 | Pass (—) | 27.34 |
| Arginine (66 mM) + methionine (10 mM) | 0.331 | Pass (—) | 25.48 |
| Arginine (66 mM) + methionine (30 mM) | 0.284 | Pass (—) | 23.17 |

Example 2

Investigation of the Effect of Different Polyols on Stability of Adalimumab in the Presence of Arginine and Methionine The effect of three different polyols stability of adalimumab (100 mg/ml) during storage at 40° C. was assessed in the presence of either methionine (30 mM) alone or a mixture of methionine (30 mM) and arginine (60 mM). Thus, the experiment also allowed a comparison of the stabilizing effect of methionine alone versus that of arginine and methionine combined. Samples were prepared by the ultracentrifugation process. Aggregation of adalimumab was assessed by SEC, visual assessment and IEX-HPLC prior to and following storage at 40° C. for 4 weeks. The effect was tested in a background formulation comprising:

sodium acetate (8 mM)

sodium chloride (34 mM)

Methionine (30 mM)

polysorbate 20 (1 mg/ml)

water for injection pH 5.0

Results are shown in Table 2. The rate of increase in HMWS was slightly lower in the presence of either propylene glycol or glycerol than in the presence of trehalose. The presence of arginine caused further improvement when added to methionine-containing formulations, further confirming the combined stabilizing effect of methionine and arginine. The presence of arginine also appeared to improve the chemical stability of adalimumab. Importantly, whilst all samples tested passed the Visual inspection test only samples containing methionine, arginine and either propylene glycol or glycerol resulted compositions that were virtually free of particles following storage at 40° C. for 4 weeks.

TABLE 2

Effect of trehalose, propylene glycol and glycerol on physical and chemical stability of adalimumab (100 mg/ml) following storage at 40° C. for 4 weeks both in the presence and in the absence of arginine (60 mM). Physical stability was assessed by the increase in % HMWS and by visual assessment. Chemical stability is expressed as decrease in the main peak on the IEX-HPLC chromatogram. All formulations contained sodium acetate (8 mM), methionine (30 mM), sodium chloride (34 mM), polysorbate 20 (1 mg/ml) and water for injection and were adjusted to pH 5.0. Pass = virtually clear solution free of visible particles; Pass (—) = very small number of minor particles; Fail = formation of particles and/or opalescence.

| Additive | Increase in HMWS (%) | Visual assessment | Decrease in IEX-HPLC main peak (%) |
|---|---|---|---|
| Trehalose (130 mM) | 0.654 | Pass (—) | 25.6 |
| Arginine (60 mM) + trehalose (130 mM) | 0.503 | Pass (—) | 24.2 |
| Propylene glycol (130 mM) | 0.620 | Pass (—) | 25.1 |
| Arginine (60 mM) + propylene glycol (130 mM) | 0.462 | Pass | 23.9 |
| Glycerol (130 mM) | 0.613 | Pass (—) | 24.5 |
| Arginine (60 mM) + glycerol (130 mM) | 0.450 | Pass | 23.6 |

Example 3

Investigation of the Effect of Methionine Concentration

The stabilizing effect of 30 mM methionine was compared with that of 60 mM methionine, both in the presence and in the absence of arginine (60 mM). Samples were prepared by the ultracentrifugation process. Aggregation of adalimumab was assessed by SEC, visual assessment and IEX-HPLC prior to and following storage at 40° C. for 4 weeks. The effect was tested in a background formulation comprising:

sodium acetate (8 mM)

sodium chloride (34 mM)

propylene glycol (130 mM)

polysorbate 20 (1 mg/ml)

water for injection pH 5.0

Results are shown in Table 3. Whilst in the absence of arginine the rate of increase in HMWS was lower in the presence of 60 mM methionine compared with 30 mM methionine, the difference was negligible in the presence of 60 mM arginine. Chemical stability was comparable in samples containing 30 mM and 60 mM methionine.

TABLE 3

Effect of methionine concentration on physical and chemical stability of adalimumab (100 mg/ml) following storage at 40° C. for 4 weeks both in the presence and in the absence of arginine (60 mM). Physical stability was assessed by the increase in % HMWS and by visual assessment. Chemical stability is expressed as decrease in the main peak on the IEX-HPLC chromatogram. All formulations contained sodium acetate (8 mM), sodium chloride (34 mM), propylene glycol (130 mM), polysorbate 20 (1 mg/ml) and water for injection and were adjusted to pH 5.0. Pass = virtually clear solution free of visible particles; Pass (—) = very small number of minor particles; Fail = formation of particles and/or opalescence.

| Additive | Increase in HMWS (%) | Visual assessment | Decrease in IEX-HPLC main peak (%) |
|---|---|---|---|
| Methionine (30 mM) | 0.620 | Pass (—) | 25.1 |
| Methionine (30 mM) + arginine (60 mM) | 0.462 | Pass | 23.9 |

TABLE 3-continued

Effect of methionine concentration on physical and chemical stability of adalimumab (100 mg/ml) following storage at 40° C. for 4 weeks both in the presence and in the absence of arginine (60 mM). Physical stability was assessed by the increase in % HMWS and by visual assessment. Chemical stability is expressed as decrease in the main peak on the IEX-HPLC chromatogram. All formulations contained sodium acetate (8 mM), sodium chloride (34 mM), propylene glycol (130 mM), polysorbate 20 (1 mg/ml) and water for injection and were adjusted to pH 5.0. Pass = virtually clear solution free of visible particles; Pass (—) = very small number of minor particles; Fail = formation of particles and/or opalescence.

| Additive | Increase in HMWS (%) | Visual assessment | Decrease in IEX-HPLC main peak (%) |
|---|---|---|---|
| Methionine (60 mM) | 0.584 | Pass (—) | 25.2 |
| Methionine (60 mM) + arginine (60 mM) | 0.458 | Pass (—) | 23.8 |

Example 4

Stability Testing of Selected Formulations

A further formulation according to the invention was prepared and its stability was tested at 30° C. The formulation was prepared by the ultracentrifugation process set forth above, and contained 100 mg/ml adalimumab. The stability of adalimumab was assessed by SEC, visual assessment, and IEX-HPLC prior to and following storage at 30° C. for 4 weeks. The composition of the formulation tested is shown in Table 4.

TABLE 4

Composition of the further formulation according to the invention.

| | Acetic acid (mM) | Methione (mM) | Arginine (mM) | Glycerol (mM) | Polysorbate 20 (mg/ml) | pH |
|---|---|---|---|---|---|---|
| Formulation A | 8 | 30 | 60 | 130 | 1 | 5.2 |

Results are shown in Table 5 below. The formulation passed the visual assessment test following storage at 30° C. for 4 weeks and only a very minor increase in high molecular weight species was observed over the same period of time. IEX-HPLC showed approximately 7% decrease in the main peak following storage at 30° C. for 4 weeks.

TABLE 5

Stability of a selected formulation following storage at 30° C. for 4 weeks. Physical stability was assessed by the increase in % HMWS and by visual assessment. Chemical stability is expressed as decrease in % main peak on the IEX-HPLC chromatogram.

| | Visual assessment (2 weeks) | Visual assessment (4 weeks) | Increase in % HMWS (2 weeks) | Increase in % HMWS (4 weeks) | Decrease in % IEX-HPLC main peak (2 weeks) | Decrease in % IEX-HPLC main peak (2 weeks) |
|---|---|---|---|---|---|---|
| Formulation A | Pass | Pass | 0.06 | 0.1 | 2.42 | 7.37 |

Pass = virtually clear solution free of visible particles;

Pass (−) = very small number of minor particles;

Fail = significant number of particles.

Example 5

Stability Testing of Selected Formulations

An additional formulation according to the invention (Formulation B) was prepared and its stability was tested at 2-8° C., 25° C. and 30° C. The formulation was prepared by the ultracentrifugation process described above and contained 100 mg/ml adalimumab. Once prepared the formulation was transferred into a syringe (0.5 ml fill with no headspace). Stability of adalimumab was assessed following storage in the pre-filled syringe at 2-8° C., 25° C. and 30° C. for up to 26 weeks by visual assessment, SEC (assessment of high molecular weight species (HMWS) and low molecular weight species (LMWS)) and IEX-HPLC (assessment of deamidated species, oxidized species and other impurities). The stability of the formulation was compared to that of the marketed adalimumab product (Humira®, 100 mg/ml) (Formulation C). In addition, to allow further comparison the stability of the formulation was compared to a composition that is identical to that of the commercial Humira® (100 mg/ml) product in terms of excipients and pH, but comprises the same adalimumab active ingredient as that used in the formulations according to the invention (Formulation D). The stability of all formulations was tested in a pre-filled syringe (0.5 ml fill). The compositions of the formulations tested are shown in Table 6.

The results are shown in Table 7 (2-8° C.), Table 8 (25° C.) and Table 9 (30° C.). The starting impurity values of the commercial Humira® (100 mg/ml) product (Formulation C) were slightly different from those observed in the product of identical composition prepared using the same adalimumab active ingredient as that used in the formulations according to the invention (Formulation D). However, the subsequent trends in the impurity increase was comparable between the two formulations. The formulation according to the invention (Formulation B) showed a lower rate of HMWS formation compared with Formulations C and D, whilst having a comparable chemical stability (i.e. increase in deamidated, oxidized and other species) to that of the Formulations C and D.

TABLE 6

Compositions of the formulations according to the invention.

| Formulation | Acetic acid (mM) | Methionine (mM) | Arginine (mM) | Glycerol (mM) | Mannitol (mM) | Polysorbate 80 (mg/ml) | Polysorbate 20 (mg/ml) | pH |
|---|---|---|---|---|---|---|---|---|
| B | 8 | 30 | 60 | 130 | | | 1 | 5.2 |
| C | | | Commercial Humira ®(100 mg/ml) product | | | | | |
| D | | | | | 230 | 1 | | 5.2 |

TABLE 7

Stability of formulations B-D following storage at 2-8° C. for up to 26 weeks.

| | 0 weeks | 4 weeks | 8 weeks | 13 weeks | 26 weeks |
|---|---|---|---|---|---|
| Formulation B | | | | | |
| Visual assessment | Pass | Pass | Pass | Pass | Pass |
| HMWS (%) | 0.38 | 0.37 | 0.39 | 0.40 | 0.43 |
| LMWS (%) | 1.65 | 1.81 | 1.90 | 1.96 | 1.95 |
| Deamidated (%) | 18.29 | 18.32 | 18.34 | 18.68 | 18.71 |
| Oxidised (%) | 3.01 | 2.99 | 3.05 | 3.04 | 2.98 |
| Other impurities (%) | 1.21 | 1.29 | 1.07 | 1.27 | 1.25 |
| Formulation C | | | | | |
| Visual assessment | Pass | Pass | Pass | Pass | Pass |
| HMWS (%) | 0.45 | 0.49 | 0.51 | 0.53 | 0.53 |
| LMWS (%) | 2.02 | 2.12 | 2.35 | 2.21 | 2.31 |
| Deamidated (%) | 16.98 | 16.99 | 17.12 | 17.50 | 17.65 |
| Oxidised (%) | 3.15 | 3.30 | 3.11 | 3.09 | 3.03 |
| Other impurities (%) | 1.26 | 1.38 | 1.28 | 1.27 | 1.47 |
| Formulation D | | | | | |
| Visual assessment | Pass | Pass | Pass | Pass | Pass |
| HMWS (%) | 0.40 | 0.45 | 0.45 | 0.50 | 0.52 |
| LMWS (%) | 1.59 | 1.78 | 1.97 | 1.86 | 2.02 |
| Deamidated (%) | 18.41 | 18.02 | 18.10 | 18.86 | 18.74 |
| Oxidised (%) | 3.01 | 3.21 | 2.98 | 3.03 | 3.05 |
| Other impurities (%) | 1.21 | 1.35 | 1.19 | 1.17 | 1.24 |

TABLE 8

Stability of formulations B-D following storage at 25° C. for up to 26 weeks.

| | 0 weeks | 4 weeks | 8 weeks | 13 weeks | 26 weeks |
|---|---|---|---|---|---|
| Formulation B | | | | | |
| Visual assessment | Pass | Pass | Pass | Pass | Pass |
| HMWS (%) | 0.38 | 0.43 | 0.54 | 0.56 | 0.63 |
| LMWS (%) | 1.65 | 2.24 | 2.70 | 3.05 | 4.22 |
| Deamidated (%) | 18.29 | 19.70 | 21.92 | 26.50 | 32.23 |
| Oxidised (%) | 3.01 | 3.67 | 4.01 | 4.20 | 5.38 |
| Other impurities (%) | 1.21 | 1.35 | 1.37 | 1.94 | 2.39 |
| Formulation C | | | | | |
| Visual assessment | Pass | Pass | Pass | Pass | Pass |
| HMWS (%) | 0.45 | 0.54 | 0.60 | 0.68 | 0.81 |
| LMWS (%) | 2.02 | 2.59 | 3.06 | 3.53 | 4.88 |
| Deamidated (%) | 16.98 | 19.03 | 21.37 | 25.69 | 31.96 |
| Oxidised (%) | 3.15 | 4.01 | 4.48 | 5.01 | 6.09 |
| Other impurities (%) | 1.26 | 1.69 | 1.72 | 2.20 | 2.85 |
| Formulation D | | | | | |
| Visual assessment | Pass | Pass | Pass | Pass | Pass |
| HMWS (%) | 0.40 | 0.55 | 0.62 | 0.76 | 1.03 |
| LMWS (%) | 1.59 | 2.04 | 2.68 | 2.90 | 3.99 |
| Deamidated (%) | 18.41 | 20.31 | 22.96 | 27.77 | 34.73 |
| Oxidised (%) | 3.01 | 3.68 | 4.04 | 4.28 | 5.20 |
| Other impurities (%) | 1.21 | 1.45 | 1.58 | 2.07 | 2.64 |

TABLE 9

Stability of formulations B-D following storage at 30° C. for up to 26 weeks.

| | 0 weeks | 4 weeks | 8 weeks | 13 weeks | 26 weeks |
|---|---|---|---|---|---|
| Formulation B | | | | | |
| Visual assessment | Pass | Pass | Pass | Pass | Pass |
| HMWS (%) | 0.38 | 0.48 | 0.54 | 0.56 | 0.63 |
| LMWS (%) | 1.65 | 2.61 | 3.41 | 4.15 | 6.06 |
| Deamidated (%) | 18.29 | 21.83 | 26.54 | 33.2 | 43.6 |
| Oxidised (%) | 3.01 | 4.31 | 4.96 | 5.44 | 6.54 |
| Other impurities (%) | 1.21 | 1.71 | 1.68 | 2.36 | 2.88 |
| Formulation C | | | | | |
| Visual assessment | Pass | Pass | Pass | Pass | Pass |
| HMWS (%) | 0.45 | 0.60 | 0.71 | 0.84 | 0.99 |
| LMWS (%) | 2.02 | 2.96 | 3.98 | 4.77 | 6.90 |
| Deamidated (%) | 16.98 | 21.18 | 25.57 | 32.52 | 42.37 |
| Oxidised (%) | 3.15 | 4.69 | 5.52 | 6.19 | 7.24 |
| Other impurities (%) | 1.26 | 2.01 | 2.61 | 3.28 | 3.02 |
| Formulation D | | | | | |
| Visual assessment | Pass | Pass | Pass | Pass | Pass |
| HMWS (%) | 0.40 | 0.62 | 0.76 | 1.03 | 1.49 |
| LMWS (%) | 1.59 | 2.45 | 3.34 | 3.94 | 5.75 |
| Deamidated (%) | 18.41 | 22.80 | 27.89 | 35.50 | 46.43 |
| Oxidised (%) | 3.01 | 4.34 | 4.88 | 5.25 | 6.12 |
| Other impurities (%) | 1.21 | 1.79 | 2.49 | 2.65 | 3.83 |

Abbreviations
HMWS—High molecular weight species
IEX-HPLC—Ion-exchange chromatography
SEC—Size exclusion chromatography
TFF—Tangential flow filtration

The invention claimed is:

1. A liquid pharmaceutical composition comprising:
    (a) 75 mg/ml to 200 mg/ml adalimumab;
    (b) 28.7 mM to 86.1 mM arginine;
    (c) 16.7 mM to 50.2 mM methionine; and
    (d) 50 mM to 200 mM propylene glycol or glycerol;
    (e) 5 mM to 10 mM acetate; and
    (f) 0.1 mg/ml to 10 mg/ml of a surfactant;
wherein the arginine:methionine molar ratio is 1:5 to 5:1; and wherein the composition has a pH of 4.5 to 5.5 and is visually clear after 30° for 4 weeks as assessed using the 2.9.20. European Pharmacopoeia Monograph.

2. The liquid pharmaceutical composition according to claim 1, which comprises glycerol.

3. The liquid pharmaceutical composition according to claim 1, wherein the composition comprises 20 mM to 40 mM methionine.

4. The liquid pharmaceutical composition according to claim 1, comprising 75 mg/ml to 125 mg/ml adalimumab.

5. The liquid pharmaceutical composition according to claim 1, wherein the composition contains at most 40 mM of a tonicifier.

6. The liquid pharmaceutical composition according to claim 1 which comprises a non-ionic surfactant.

7. The liquid pharmaceutical composition according to claim 1 consisting-of:
    (a) 75 mM to 200 mg/ml adalimumab;
    (b) 50 mM to 70 mM L-arginine;
    (c) 20 mM to 40 mM L-methionine;
    (d) 100 mM to 150 mM glycerol or propylene glycol;
    (e) 5 mM to 10 mM acetate;
    (f) 20 mM to 40 mM sodium chloride;
    (g) 0.5 mg/ml to 2 mg/ml polysorbate 20 or poloxamer 188; and (h) a diluent;
wherein the composition has a pH between 4.8 and 5.2;
or consisting of:
    (a) 75 mg/ml to 200 mg/ml adalimumab;
    (b) 50 mM to 70 mM L-arginine;
    (c) 20 mM to 40 mM L-methionine;
    (d) 100 mM to 150 mM glycerol or propylene glycol;
    (e) 5 mM to 10 mM acetate;
    (f) 0.5 mg/ml to 2 mg/ml polysorbate 20 or poloxamer 188; and (g) a diluent;
wherein the composition has a pH between 5.0 and 5.4.

8. The liquid pharmaceutical composition according to claim 7, which comprises a sodium acetate buffer.

9. The liquid pharmaceutical composition according to claim 1 consisting of:
    (a) 100 mg/ml adalimumab;
    (b) 60 mM L-arginine;
    (c) 30 mM L-methionine;
    (d) 130 mM glycerol or propylene glycol;
    (e) 8 mM acetate;
    (f) 30 mM sodium chloride;
    (g) 1 mg/ml polysorbate 20 or poloxamer 188; and (h) a diluent;
wherein the composition has a pH of 5.0;
or consisting of:
    (a) 100 mg/ml adalimumab;
    (b) 60 mM L-arginine;
    (c) 30 mM L-methionine;
    (d) 130 mM glycerol or propylene glycol;
    (e) 8 mM of an acetate;
    (f) 1 mg/ml polysorbate 20 or poloxamer 188; and (g) a diluent;
wherein the composition has a pH of 5.2.

10. The liquid pharmaceutical composition according to claim 9, which comprises a sodium acetate buffer.

11. The liquid pharmaceutical composition according to claim 1, comprising 100 mg/ml to 125 mg/ml adalimumab.

12. The liquid pharmaceutical composition according to claim 1, comprising 100 mg/ml to 200 mg/ml adalimumab.

13. The liquid pharmaceutical composition according to claim 1, wherein the composition comprises an acetate buffer system formed by basification of acetic acid.

14. The liquid pharmaceutical composition according to claim 1, wherein the composition comprises an acetate buffer system formed without generating sodium chloride.

15. The liquid pharmaceutical composition according to claim 1, wherein the composition contains at most 40 mM of a tonicifier.

16. The liquid pharmaceutical composition according to claim 15, wherein the composition contains at most 40 mM of sodium chloride.

17. The liquid pharmaceutical composition of claim 1, wherein the arginine concentration is 50 mM to 70 mM.

18. The liquid pharmaceutical composition of claim 1, wherein the methionine concentration is 20 mM to 100 mM.

19. The liquid pharmaceutical composition of claim 1, wherein the combined concertation of arginine and methionine is 50 mM to 130 mM.

20. The liquid pharmaceutical composition of claim 1, wherein the combined concertation of arginine and methionine is 80 mM to 100 mM.

21. The liquid pharmaceutical composition of claim 1, which comprises propylene glycol.

22. The liquid pharmaceutical composition of claim 1, wherein the composition comprises 100 mM to 200 mM propylene glycol or glycerol.

23. The liquid pharmaceutical composition of claim 1, wherein the composition comprises 100 mM to 150 mM propylene glycol or glycerol.

\* \* \* \* \*